United States Patent
Sun et al.

(10) Patent No.: US 6,657,050 B1
(45) Date of Patent: *Dec. 2, 2003

(54) CHIMERIC VIRAL-NEUTRALIZING IMMUNOGLOBULINS

(75) Inventors: Cecily R. Y. Sun, Bellaire, TX (US); Bill N. C. Sun, Bellaire, TX (US); Michael S. C. Fung, Houston, TX (US); Tse Wen Chang, Houston, TX (US); Nancy T. Chang, Houston, TX (US)

(73) Assignee: Tanox, Inc., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/015,248

(22) Filed: Feb. 5, 1993

Related U.S. Application Data

(63) Continuation-in-part of application No. 07/898,383, filed on Jun. 9, 1992, now abandoned, which is a continuation of application No. 07/197,766, filed on May 23, 1988, now abandoned, which is a continuation-in-part of application No. 07/137,831, filed on Dec. 24, 1987, now abandoned, which is a continuation-in-part of application No. 07/057,445, filed on May 29, 1987, now abandoned.

(51) Int. Cl.$^7$ ................................................. C07K 1/28

(52) U.S. Cl. ............................. 530/388.35; 530/387.3; 530/388.1

(58) Field of Search ...................... 530/387.3, 388.35, 530/387.9, 388.1; 424/130.1, 133.1, 139.1, 159.1

(56) References Cited

U.S. PATENT DOCUMENTS

| | | | |
|---|---|---|---|
| 4,664,911 A | 5/1987 | Uhr et al. | |
| 4,725,669 A | 2/1988 | Essex et al. | |

FOREIGN PATENT DOCUMENTS

| | | |
|---|---|---|
| EP | 0125023 | 4/1984 |
| EP | 0129434 | 6/1984 |
| EP | 0171496 | 3/1985 |
| EP | 0171496 | 2/1986 |
| EP | 0193284 | * 3/1986 |
| EP | 0214709 | 4/1986 |
| EP | 0185444 | 6/1986 |
| EP | 0199301 | 10/1986 |
| EP | 0248534 | 5/1987 |
| EP | 0295803 | 12/1988 |
| GB | 2137631 A | 3/1984 |
| GB | 2196634 B | 5/1991 |
| WO | WO86/01533 | 9/1985 |
| WO | 8601533 | * 3/1986 |
| WO | WO86/02383 | 4/1986 |
| WO | WO87/02775 | 5/1987 |
| WO | WO87/02671 | 7/1987 |

OTHER PUBLICATIONS

Liou et al. Journal of Immunology 143 3967–3975 1989.*
TiBTECH Feb. 1993 vol. 11, p. 42.*
Legrain et al. J. Virology 60:1141–1144 1986.*
Morrison, S.L., Science vol. 229 pp. 1203–1207, 1985.*
Robey et al. PNAS USA vol. 83 pp 7023–7027, 1986.*
Lasky et al. Science vol. 223, pp 209–212, 1986.*
Chanh et al. Eur. J. Immunol. 16: 1465–68 1986.*
Lafon et al. J. Gen. Virol. 64: 8431–51 1983.*
Dreesman et al. J. Cellular Biochem, Suppl. 11D 1987 p. 34.*
McDougal et al. "HIV Binding to CD21 Molecule . . . " J. Cellular Biochemistry Supp.11D (1987).
Gosting et al. "Monoclonal Antibodies to 8P110 and gp 41 . . . " J Clinical Microbiology 25(5) 845–848 1987.
M. Robert–Guroff, et al., Nature, 316: 72–74 (1985).
Weiss et al. "Variable and Conserved Neutralization Antigens of Human Immunodeficiency Virus" Nature 324: 572–75 (1986).
Ho et al. "Human Immunodeficiency Virus Neutralizing Antibodies Recognize Several Conserved Domains on the Envelope Glycoproteins" J. Virol. 2024–8 (1987).
J.D. Lifson et al., Nature, 323: 725–728 (1986).
S.D. Putney, et al., Science, 234: 1392–1395 (1986).
Gottlieb et al. Current Typics in AIDS; Chapter 12 (1987).
"Expression of the Fusion Protein of Human Respiratory Syncytial Virus from Recombinant Vaccinia Virus Vectors and Protection of Vaccinated Mice," vol. 61, No. 2 Journal of Virology 293–301 (1987); G.W. Wertz et al.
"Expression of the HTLV–III Envelope Gene by a Recombinant Vaccinia Virus," 320 Nature 535–540 (1986): S. Chakrabarti et al.
"Binding of HTLV–III/LAV to T4+ T Cells by a Complex of the 110k Viral Protein and the T4 Molecule," 232 Science 382–385 (1986); J.S. McDougal et al.
"Neutralization of Human T–Lymphotropic Virus Type III by Sera of AIDA and AIDS–Risk Patients," 316 Nature 69–72 (1985); Weiss et al.
"Neutralization of HTLV–III/LAV Replication by Antiserum to Thymosin alpha$_1$," 232 Science 1135–1137 (1986); Sarin et al.
"Human Immunodeficiency Virus Contains an Epitope Immunoreactive with Thymosin Alpha$_1$ and the 30–Amino and Synthetic p17 Group–Specific Antigens Peptide HGP–30," 84 Proc. Natl. Acid. Sci. USA 2951–55 H. Naylor, et al.
"AIDS Virus ENV Protein Expressed From a Recombinant Vaccinia Virus," 4 Bio/Technology 790–795 (1986); M.P. Kieny et al.

(List continued on next page.)

Primary Examiner—Larry Ronald Helms
(74) Attorney, Agent, or Firm—Cheryl A. Liljestrand

(57) ABSTRACT

Chimeral viral-neutralizing, particularly HIV-neutralizing, immunoglobulins made up of a non-human antigen binding region and a human constant region are described.

3 Claims, 6 Drawing Sheets

OTHER PUBLICATIONS

"The CD4 (T4) Antigen is an Essential Component of the Receptor for the AIDS Retrovirus," 312 Nature 763–67 (1984); Dagleish et al.

"Role of the HTLV–III/LAV Envelope in Syncytium Formation and Cytopathicity," 322 Nature 470–474 (1986); Sodroski et al.

"Chimeric Antibodies with 17–1A–Derived Variable and Human Constant Regions," 5 Hybridoma Suppl. 1 (1986); L.K. Sun et al.

"Chimeric Antibodies," vol. 4 No. 3 Biotechniques 214–221 (1986); V.T. Oi & S.L. Morrison "T–Lymphocyte Priming and Protection Against Friend Leukemia by Vaccinia–Retrovirus env Gene Recombinant," 234 Science 728–731 (1986) : P.L. Earl, et al.

"A Chemical Technique for the Preparation of Bispecific Antibodies from Fab Fragments of Mouse Monoclonal $IgG_1$," Vol 4 No 5 Biotechniques 424–427 (1986) M. Brennan.

"Restricted Neutralization of Divergent Human T–Lymphotropic Virus Type III Isolates by Antibodies to the Major Envelope Glycoprotein," 83 Pro. Natl. Acad. Sci. USA 9709–9713 (1986); Mathews et al.

"Infection of HTLV–III LAV in HTLV–1–Carrying Cells MT–2 and MT–4 and Application in a Plaque Assay," 229 Science 563–566 (1985); S. Harada, et al.

* cited by examiner

FIG. 6

CHIMERIC VIRAL-NEUTRALIZING IMMUNOGLOBULINS

RELATED APPLICATION

This application is a CIP of U.S. Ser. No. 07/898,383 Jun. 9, 1992 ABN which is a CON of U.S. Ser. No. 07/197,766 May 23, 1988 ABN which is a CIP of U.S. Ser. No. 07/137,861 Dec. 24, 1987 ABN which is a CIP of U.S. Ser. No. 07/057,445 May 29, 1987 ABN.

BACKGROUND OF THE INVENTION

The use of monoclonal antibodies for therapy has gained increasing interest in recent years. The ability to influence an individual's immune state by administering immunoglobulin of appropriate specificity has been considered a powerful approach to disease control and prevention. Therapeutic efficacy of certain monoclonal antibodies in anti-tumor treatment has been documented. See e.g., Sears, H. F. et al., (1984) *J. Biol. Resp. Modif.* 3:138.

Viral specific antibodies can be therapeutically useful for treatment of viral infections. Antibodies directed against some components of a virus can neutralize the virus. Antibodies which fix complement (C1–C9) cause lysis of cells carrying viral antigens or directly damage enveloped viruses. Furthermore, antibodies that bind to Fc receptors on the surface of phagocytic cells can also cause antibody-dependent cell-mediated cytotoxicity of virus-infected cells.

Recently, monoclonal antibodies have been developed against the exterior glycoprotein gp120 of the human immunodeficiency virus (HIV), the causative agent of acquired immunodeficiency syndrome (AIDS). See, Fung, S. C. et al., *BioTechnology* 5:940 (1987). The antibodies are capable of inhibiting the infection of susceptible T cells by free virions. The antibodies also inhibit the fusion between HIV-infected cells and uninfected cells which results in the formation of multinucleated giant cells (syncytia), a mechanism implicated as a major route of viral transmission and T cell death. These HIV-neutralizing antibodies have applications in therapy and prevention of AIDS.

Most presently available monoclonal antibodies, including antiviral monoclonal antibodies, are murine antibodies. The production of human antibodies by somatic cell fusion is generally difficult. Techniques for production of monoclonal antibodies in the mouse, however, are well established and allow for preparation of monoclonal antibodies against virtually any antigen.

Murine antibodies, however, have several drawbacks which impede their use in human therapy. As foreign proteins, murine antibodies often evoke counteracting immune reactions which may reduce or destroy their therapeutic effectiveness. In addition, murine antibodies can elicit allergic or hypersensitivity reactions in patients. Unfortunately, the need for readministration in therapy increases the likelihood that these immune reactions will occur in patients.

One way to ameliorate the problems associated with the in vivo use of a murine antibody is to convert the murine antibody to a "chimeric" antibody. The chimeric antibody consists of the variable region of the murine antibody joined to a human constant region. See, e.g., Morrison, S. L. et al. (1984) "Chimeric Human Antibody Molecules: Mouse Antigen-binding Domains with Human Constant Region Domains" *Proc. Natl. Acad. Sci. USA* 81:6851; Neuberger, M. S. and Rabbits, T. H. "Production of Chimeric Antibodies" PCT Application No. PCT/GB85 00392. Because the chimeric antibody has a human constant region (the region which is largely responsible for inducing immune response against antibody), it is less likely to evoke an anti-murine immune response in humans. Furthermore, the human constant region may provide for an antibody with a longer half life and better effector function in humans.

A number of studies have described chimeric murine/human immunoglobulins. See, e.g., Sun, L. K. et al., (1987) *Proc. Natl. Acad. Sci. USA* 84:214; Liu, A. Y. et al., (1987) *J. Immunol.* 139:3521; Sahagan, B. G. et al., (1986) *J. Immunol.* 137:1066, Liu, A. Y. et al., (1987) *Proc. Natl. Acad. Sci. USA* 84:3439.

SUMMARY OF THE INVENTION

This invention pertains to chimeric viral neutralizing immunoglobulins, particularly HIV-neutralizing immunoglobulins, comprising a viral-specific antigen binding (variable) region of nonhuman origin and a constant region of human origin. The chimeric immunoglobulins, prepared by genetic engineering techniques, retain the viral neutralizing activity of the parent, nonhuman immunoglobulin from which they are derived. The chimeric immunoglobulins are useful for immuno-therapy of viral-mediated diseases such as AIDS.

BRIEF DESCRIPTION OF THE DRAWINGS

FIG. 6 shows the neutralizing activities of chimeric antibody on the infection of H9 cells by HIV-1. Cell-free culture supernatants were collected at day 14 for HIV-1 specific antigen capture assays after the H9 cells were challenged with HIV-1 in the absence and in the presence of antibody tested. Each concentration of the antibodies was tested in triplicate. The inhibition of HIV-1 infection was calculated by comparing the optical densities obtained in the antigen capture assays of cultures infected with the virus in the presence of antibody to the negative control without added antibody. The antibodies tested were BAT123 (○), Chimeric antibody cAG1-51-4 (●), and a non-reactive murine anti-hcG antibody (Δ).

DETAILED DESCRIPTION OF THE INVENTION

Figure 1:
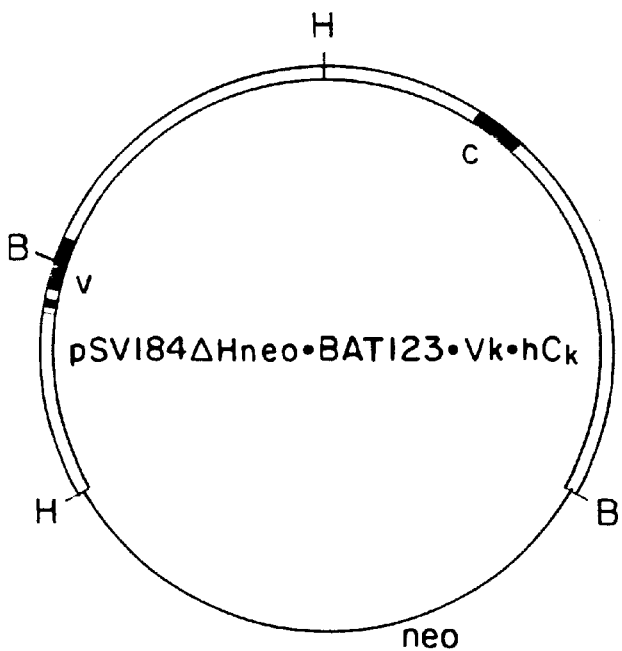
FIG. 1 is a schematic depiction of the structure of chimeric genes encoding a light and a heavy chain for a chimeric HIV-neutralizing antibody. (A) Plasmid pSV184ΔHneo. BAT123$V_\kappa$·h$C_\kappa$ contains a chimeric light chain gene construct consisting of a 4.4 kbp Hind III fragment of mouse $V_\kappa$ gene fused with the human $C_\kappa$ gene. This plasmid contains a neo selection marker. (B) Plasmid pSV2ΔHgpt.BAT123$V_H$·h$C_{\gamma 1}$ contains a chimeric heavy chain gene construct consisting of a 4.5 Kbp Eco RI fragment of mouse $V_H$ gene fused with the human $C_{\gamma 1}$ gene. The plasmid carriers an Eco gpt selection marker. B: Bam HI, E: Eco RI, H: Hind III, S: Sal I, V: variable region gene, C: constant region.
Figure 1:
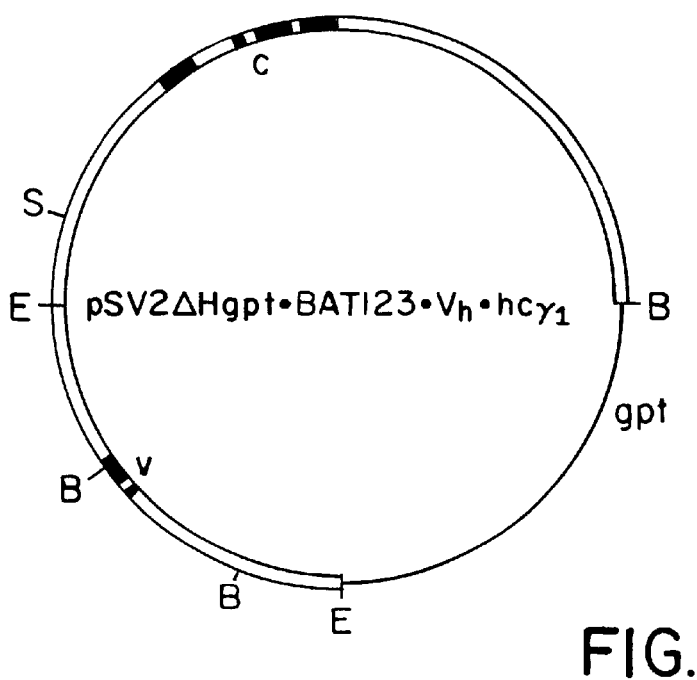

The chimeric immunoglobulins of this invention are made up of chimeric heavy and light immunoglobulin chains. Each chimeric chain is a contiguous polypeptide that has a nonhuman variable region and a human constant region. The chimeric heavy and light chains are associated to form a molecule with a functional antigen binding region.

The chimeric immunoglobulins of this invention can be monovalent, divalent or polyvalent. Monovalent immunoglobulins are dimers (HL) formed of a chimeric heavy chain (H) associated (through disulfide bridges) with a chimeric light chain (L). Divalent immunoglobulins are tetramers ($H_2L_2$) formed of two associated dimers. Polyvalent antibodies can be produced, for example, by employing heavy chain constant region which aggregate (e.g., mu type constant regions).

The chimeric immunoglobulins can be produced as antigen binding fragments. Fragments such as Fv, Fab, Fab' or $F(ab')_2$ can be produced by employing appropriately truncated heavy chain constant regions.

The variable regions of the chimeric immunoglobulins are derived from nonhuman immunoglobulins having the desired viral specificity and viral-neutralizing properties. In preferred embodiments, the parent antiviral immunoglobulin neutralize different types, strains and isolates of a virus. This provides crossprotection against viruses of different types, stains and isolates that are encountered in viral populations.

Important pathogenic viruses for which chimeric viral-neutralizing antibodies can be produced are HIV, human T cell lymphotropic virus I (a causative agent of adult T cell leukemia), and hepatitis B virus.

HIV-neutralizing immunoglobulins are described in U.S. patent application Ser. No. 137,861, filed Dec. 24, 1987 (abandoned), a continuation-in-part of U.S. patent application Ser. No. 057,445, filed May 29, 1987 (abandoned), and in Fung, et al. supra. (The teachings of these references are incorporated by reference herein.) These HIV)-neutralizing antibodies specifically react with the glycoprotein gp120 of HIV-1; they inhibit the infection of T cells by free virions and inhibit infection of T cells by fusion with HIV-infected cells. The antibodies are preferred because they are cross-neutralizing, i.e. they neutralize different strains and isolates of HIV-1. For example, antibody BAT123 is especially preferred because of its neutralizing activity and cross strain reactivity. The BAT123 antibody inhibits with an $IC_{50}$ of less than 10 ng/ml, the infection of a susceptible human T cell line, H9, by HTLV-III B strains at 20 times $TCID_{50}$ in a nine day assay. The antibody also inhibits some other cloned HIV-1 strains and it inhibits the in vitro replication of broad, freshly isolated field HIV-1 samples from patients. BAT123 was deposited in the general depository at the American Type Culture Collection, Rockville, Md., on Apr, 20, 1990, and assigned Accession No. HB 10438. BAT267 was was deposited in the general depository at the American Type Culture Collection, Rockville, Md., on Dec. 14, 1990, was assigned Accession No. HB 10626.

The heavy chain constant region for the chimeric immunoglobulins can be selected from any of the five isotypes alpha, delta, epsilon, gamma or mu. Heavy chains of various subclasses (such as the IgG subclasses 1–4) can be used. The different classes and subclasses of heavy chains are involved in different effector functions and thus, by choosing the type of heavy chain constant region, chimeric antibodies with desired effector function can be produced. The light chains can have either a kappa or lambda constant chain.

The chimeric immunoglobulins of this invention are produced by genetic engineering techniques. Appropriate recipient cells are transfected with nucleic acid constructs, preferably DNA, encoding the desired chimeric light or heavy chain. In general, DNA constructs for each of the light and heavy chain components of the chimeric immunoglobulin comprise a fused gene comprising a first DNA segment which encodes at least the functional portion of the variable region linked to a second DNA segment encoding at least a part of a constant region. The fused gene is assembled in or inserted into an expression vector for transfection of the appropriate recipient cells.

In preferred embodiments the fused gene construct will comprise a functionally rearranged gene encoding a variable region of a chain of a viral-neutralizing immunoglobulin linked to a gene encoding a constant region of an immunoglobulin chain. The construct will also include the endogenous promoter and enhancer for the variable region encoding gene. For example, the variable region encoding genes can be obtained as DNA fragments comprising the leader peptide, the VJ gene (functionally rearranged variable (V) regions with joining (J) segment) for the light chain or VDJ gene for heavy chain, and the endogenous promoter and enhancer for these genes. These variable region genes can be obtained from antibody-producing cells that produce the desired viral-neutralizing antibody by standard DNA cloning procedures. See *Molecular Cloning: A Laboratory Manual*. T. Maniatis et al. Cold Spring Harbor Laboratory (1982). Screening of the genomic library for the functionally rearranged variable region can be accomplished with the use of appropriate DNA probes such as DNA segments containing the mouse germline J region DNA sequences and sequences downstream. Identification and confirmation of the correct clones are then achieved by DNA sequencing of the cloned genes and comparison of the sequence to the corresponding sequence of the full length, properly spliced mRNA. The DNA fragment containing the functionally rearranged variable region gene is linked to a DNA fragment containing the gene encoding the desired constant region (or a portion thereof).

Genes encoding antibody light and heavy chains can be obtained generally from immunoglobulin-producing lymphoid cells. Hybridoma cell lines producing antibody against a desired virus can be made by standard procedures.

See, Koprowski et al., U.S. Pat. No. 4,196,265. In general, these entail challenging a animal with a virus or a purified or partially purified viral antigen, fusing antibody-producing cells taken from the immunized animal with compatible myeloma cells to form hybridoma cells, cloning the resulting hybridoma cells and selecting clones which produce antibody against the virus. The hybridoma clones can be screened for the production of viral-neutralizing antibody by tests for neutralizing activity for the particular virus. For example, several in vitro assays for HIV-neutralizing activity are described in U.S. patent application Ser. No. 137,861, supra, and in the Exemplification below.

Human constant regions can be obtained from antibody-producing cells by standard gene cloning techniques. Genes for the two classes of human light chains and the five classes of human heavy chains have been cloned, and thus, constant regions of human origin are readily available from these clones. Chimeric immunoglobulin fragments such as the monovalent Fv, Fab or Fab' fragments or the divalent F(ab')$_2$ fragment can be prepared by designing a chimeric heavy chain gene in truncated form. For example, a chimeric gene encoding a F(ab')$_2$ heavy chain would include DNA sequences encoding the CH$_1$ domain and at least sulfhydryl-containing part of the hinge region of the heavy chain.

The fused genes encoding either the light or heavy chains are assembled or inserted into expression vectors for incorporation into a recipient cell. Suitable vectors for the chimeric gene constructs include plasmids of the types pBR322, pEMBL, and pUC. The introduction of gene constructs into plasmid vectors can be accomplished by standard procedures.

In preferred embodiments, the expression vector is designed to contain two selectable genetic markers, one for selection in a prokaryotic (bacterial) system and the other is for selection in a eukaryotic system. The fused genes can be produced and amplified in a bacterial system and subsequently incorporated and selected for in eukaryotic cells. Examples of selectable genes for a prokaryotic system are the gene which confers ampicillin resistance and the gene which confers chloramphenicol resistance. Two genes for selection of eukaryotic transfectants are preferred (i) the xanthine-guanine phosphoribosyl-transferase gene (designated gpt) and (ii) the phosphotransferase gene from Tn5 (designated neo). Selection with gpt is based on the ability of the enzyme encoded by this gene to use xanthine as a substrate for purine nucleotide synthesis; the analogous endogenous enzyme cannot. In a medium containing xanthine and mycophenolic acid which blocks the conversion of inosine monophosphate to xanthine monophosphate, only cells expressing the gpt gene can survive. The product of the neo blocks the inhibition of protein synthesis in eukaryotic cells caused by the antibiotic G418 and other antibodies of its class.

The chimeric light and heavy chain genes can be placed in two different expression vectors which can be used to cotransfect a recipient cell. In this case, each vector is designed to have a different selectable gene for eukaryotic transfectants. This allows cotransfection of the recipient cell and selection of cotransfected cells (i.e. cells that have received both vectors). Selection of co-transfected cells is accomplished by selection for both selectable markers, which can be done simultaneously or sequentially.

Recipient cell lines are generally lymphoid cells. The preferred recipient cell is a myeloma. Myelomas can synthesize, assemble and secrete immunoglobulins encoded by transfected genes and they can glysosylate protein. A particularly preferred recipient cell is the myeloma Sp2/0 which normally does not produce endogenous immunoglobulin. When transfected, the cell will produce only immunoglobulin encoded by the transfected gene constructs. Transfected myelomas can be grown in culture or in the peritoneum of mice where secreted immunoglobulin can be recovered from ascites fluid. Other lymphoid cells such as B lymphocytes or hybridomas can be used as recipient cells.

There are several methods for transfecting lymphoid cells with vectors containing chimeric L and H chain genes. A preferred way of introducing a vector into lymphoid cells is the calcium phosphate precipitation procedure described by Graham and van der Eb, (1973) *Virology* 52:456. Another way is by electroporation. In this procedure, recipient cells are subjected to an electric pulse in the presence of the DNA to be incorporated into the cell. See e.g., Potter, et al. (1984) *PNAS* 81:7161. Another way to introduce DNA is by protoplast fusion. A lysozyme is used to digest cell walls from bacteria which contain the recombinant vector with the chimeric chain gene to produce spheroplasts. The spheroplasts are fused with the lymphoid cells in the presence of polyethylene glycol. After protoplast fusion, the transfectants are selected and isolated. (Oi, et al., (1983) *PNAS* 80:825). Finally, the DEAE-dextran procedure described by Cullen, et al., (1984) *Nature* 307:241 can also be used.

The chimeric viral-neutralizing immunoglobulins of this invention are useful for antiviral therapy, prophylaxis and diagnosis. Direct in vivo treatment with the chimeric immunoglobulins of this invention entails administering them internally preferably by intravenous injection in a pharmaceutically acceptable vehicle such as sterile saline. The antibodies can be administered in conjunction with other anti-viral agents.

A variant of immunotherapy is protection through passive immunization. In this mode, the antibody is administered to persons at risk of contracting viral infection in order to protect against infection.

Chimeric HIV-neutralizing immunoglobulins can be used to treat AIDS patients or persons who are HIV carriers. As mentioned above, chimeric immunoglobulins (of this invention formed, for example, from HIV-neutralizing immunoglobulins such as BAT123) are capable of neutralizing different strains and isolates of HIV-1. Further, these immunoglobulins can inhibit transmission of the virus be syncytia formation. The chimeric immunoglobulins can be administered to reduce viral load in an AIDS patient and to retard further progression of the disease. The immunoglobulins can be administered in conjunction with other anti-AIDS agents such as AZT. In addition, several different chimeric HIV-neutralizing immunoglobulins can be administered together.

In certain patient populations, passive immunization with the chimeric HIV-neutralizing immunoglobulins may be appropriate. In this procedure, patients who are asymptomatic (not yet showing symptoms of AIDS or ARC), or who are seronegative but in a high risk group, are treated to inhibit infection. The targets includes fetuses carried by or babies born to HIV-1-carrier mothers and health professionals working with AIDS patients, or blood products, such as dentists and nurses.

Another use for the monoclonal antibodies (chimeric and murine) of the invention is in detecting the presence of HIV-1 or infected cells, or quantifying the concentration of HIV-1 or of infected cells, present in a biological fluid or an unknown sample. This utility is useful for diagnosis of HIV-1 infection and detection of HIV-1 contamination in a culture or another sample. These antibodies can be used in standard assay formats, such as the ELISA format or the radioimmunoassay format described below.

(i) Detecting HIV-1 virions with a Radioimmunoassay

The monoclonal antibodies of the invention, either alone or in combination, can be immobilized on inert solid phase, for example, the inside of a test tube. A sample of the patient's serum is added to the tube, together with a known amount of peptide known to be reactive with the antibody (three such peptides are shown on page 68, last three lines). The peptide is labelled with a radioactive isotope such as radioactive iodine. Any HIV antigen in the patient's serum will compete with the labelled peptide for binding with the HIV antibodies. The excess liquid is removed, the test tube washed, and the amount of radioactivity measured. A positive result (that the patient's serum contains HIV antigen) is indicated by a low radioactivity count left in the tube, as compared with a control.

(ii) Detecting HIV-1 virions with an ELISA

The monoclonal antibodies of the invention, either alone or in combination, can be immobilized on inert solid phase, for example, the inside of a test tube, or on magnetic beads, either directly or indirectly through a cross-linking agent or a specific binding agent (e.g. protein A or goat anti-mouse IgG). The biological fluid test samples are then incubated with the antibody-coated matrices. HIV-1 virions or gp120 reactive with the antibodies will bind to the matrices. The bound virions or gp120 can then be detected with either monoclonal or polyclonal anti-HIV-1 antibodies, which can then be reacted with enzyme-linked secondary detecting antibodies for quantitation based on color reaction. Alternatively, the captured virions can be detected by other means, e.g. fluorescence, chemiluminescence, or PCR.

(iii) Detecting HIV-1-Infected Cells in a Sample

The monoclonal antibodies of the invention can be used to detect and to quantitate the HIV-1-infected cells in patient blood samples by direct or indirect immunofluorescence procedures. Patient serum is incubated with the antibodies of the invention. After incubation, the tubes are spun, the supernatant is withdrawn, and the cells are washed three times with a mixture of RPMI 1640, containing 2% fetal calf serum and 0.1% sodium azide. The tubes are then tapped to loosen the cell pellet.

Goat anti-mouse IgG conjugated with fluorescein isothiocyanate (FITC) is added to each test tube. This labeled antibody will bind to any monoclonal antibodies which have attached to HIV-1 infected H9 cells and provide a means for identifying these monoclonal antibodies.

The tubes are again incubated for thirty minutes at room temperature. The tubes are centrifuged, and the cells are washed with the same medium as before. The cells are then resuspended in PBS, placed onto individual slides and cover-slipped. The cells are viewed with a fluorescence microscope.

The invention is illustrated further by the following exemplification.

EXEMPLIFICATION

Cloning and Identification of the Functionally Rearranged $V_L$ and $V_H$ Genes of BAT123

The cloning of the functionally rearranged $V_L$ and $V_H$ genes of BAT123 was accomplished by the screening of BAT123 genomic libraries using appropriate molecular probes in a strategy similar to that described by Oi and Morrison (*Biotechniques*, 4:214–221). The identification and final verification of the cloned gene segments was achieved by the aid of the nucleotide sequences of mRNA's for BAT123 immunoglobulin molecules. The rationale is based on the fact that only when a variable region gene segment is appropriately joined to the J region gene in the case of κ chain rearrangement or appropriate VDJ joining occurs in the case of heavy chain rearrangement, is the full length and properly spliced immunoglobulin mRNA synthesized in the antibody producing cells.

The sequences of these mRNA's, determined either by direct sequencing of the mRNA molecule or from the cDNA clones are therefore most suitable to serve as a guide for the selection and verification of the functionally rearranged variable region genes. Any gene segment containing sequences identical to the RNA sequence can be considered functionally rearranged.

The sequences of the mRNA molecules corresponding to the variable regions were determined by a primer extension/dideoxynucleotide termination method with the use of mRNA prepared from the polysomes of the BAT123 hybridoma cells. This direct RNA sequencing approach eliminates the intermediate cDNA cloning step in the conventional approach to derive the mRNA sequence; hence, it provides a relatively fast way to determine the RNA sequence.

The primers used for this RNA sequencing were 5'dTGGATGGTGGGAAGATG3' for light chain mRNA and 5'dGGCCAGTGGATAGAC3' for heavy chain mRNA (both primers were obtained from Pharmacia, Nutley, N.J.). These oligonucleotides were complementary to the mRNA sequences in the constant regions at positions proximal to the junctions of J and C regions of the molecules. Primer extension was accomplished with the use of AMV reverse transcriptase and terminated by dideoxynucleotides. The nucleotide sequence of mRNA's was determined by the gel electrophoresis and subsequent autoradiography.

A genomic DNA library for BAT123 cells was constructed in lambda phage vector λ2001 (Karin, J., Natthes, W. D. H., Gait, M. J., Brenner, S. (1984) *Gene* 32:217–274). High molecular weight genomic DNA from BAT123 hybridoma cells was partially digested with restriction endonuclease Sau 3AI and size fractionated on a 10–40% sucrose density gradient. DNA fragments of 18–23 kilobase pairs (Kbp) were ligated with λ2001/BamH1 arms (Stratagene Cloning Systems, La Jolla, Calif.). and packaged by using Gigapack Gold packaging extracts (Stratagene). This genomic library was first screened for the functionally rearranged variable region gene of BAT123 light chain ($V_L$). The probes used for this screening included a 2.7 Kbp Hind III DNA fragment containing all of the mouse germline kappa (κ) chain joining regions J1–J5 ($J_\kappa$ probe; Max, E. E., Maizel, J. V., and Leder, P. (1981) *J. Biol. Chem.* 256:5116–5120) and two oligonucleotide probes $V_\kappa$-1 and $V_\kappa$-2 derived from the nucleotide sequence of BAT123 light chain mRNA. The sequences of these oligonucleotide probes are $V_\kappa$-1: 5'-dTTTGCTGACAGTAATAGG3' and $V_\kappa$-2: 5'dATATAACTATCACCATCA3'. The probes were synthesized by using the phosphoramidite chemistry on an Applied Biosystems DNA synthesizer model 381.

Approximately $5\times10^5$ phage recombinants were screened initially with $^{32}$P-labeled mouse $J_\kappa$ DNA probe. Plaque hybridizations were carried out in 5×SSC with 50% (v/v) formamide at 42° C. for 16 hours (1×SSC=0.15M NaCl, 0.015M sodium citrate). Final washes were in 0.2×SSC/0.1% SDS at 65° C. Two positive clones were obtained. They were subsequently screened with the use of $^{32}$P-labeled oligonucleotide probes $V_\kappa$-1 and $V_\kappa$-2. Hybridization with the oligo-probes were carried out in 5×SSC at 37° C. for 18 hours and washes were carried out in 2×SSC/0.1% SDS at room temperature. One of these clones, $V_\kappa$123-23 was shown to hybridize with the $J_\kappa$ DNA probe and both oligonucleotide probes. DNA sequence determination of this clone by the dideoxy-nucleotide termination method showed that it carried a $V_L$ gene segment with sequence identical to that determined from BAT123 light chain mRNA. This clone was used in the subsequent construction of the mouse/human chimeric L chain gene.

For the cloning of the functionally rearranged variable region genes for BAT123 heavy chain ($V_H$), partial genomic libraries were prepared. Genomic Southern blots of the EcoRI digest with the $J_H$ probe (see below) had previously revealed 2 potentially functionally rearranged $V_H$ genes in BAT123, one being 7.5 Kbp and the other 4.5 Kbp, in addition to the 6.6 Kbp fragment which was presumably derived from the fusion parent of BAT123, i.e. NS-1 cells. Two partial libraries containing these DNA bands were prepared. High molecular weight DNA was digested with EcoRI to completion and fractionated on a 0.7% agarose gel. DNA fragments of the size 4–6 Kbp and 6–9 Kbp were isolated and ligated with lambda vector λgtWESλB (Leder, P., Timeier, D., and Enquiest, L. (1977) *Science* 196:175–177). The ligated DNAs were packaged and recombinant plaques were screened. The probes used included a 2 Kbp BamHI-EcoRI DNA fragment containing the mouse H chain joining regions J3 and J4 ($J_H$ probe; Gough, N. M. and Bernard, O. (1981) *Proc. Natl. Acad. Sci. USA* 78:509–513) and an oligonucleotide probe VH-1, 5'dAGTGTGGCTGTGTCCTC3' derived from BAT123 mRNA sequence. The hybridization conditions for these probes were as described above for κ chain. Screening of these two EcoRI partial libraries with $J_H$ probe resulted in the isolation of 3 independent phage clones containing a 7.5 Kbp, 6.6 Kbp or a 4.5 Kbp DNA fragment. Subsequent hybridization using oligonucleotide probe VH-1 revealed that only the phage clone containing 4.5 Kbp insert, clone $V_H$123-E3, hybridized with the probe. DNA sequencing of this clone showed that it contained a $V_H$ sequence identical to that from $V_H$ mRNA of BAT123. This clone was used in the construction of the mouse-human chimeric H chain gene.

Fusion of Murine V with Human C exons and Introduction into Murine Myeloma Cells The functionally rearranged L and H chain V genes isolated from BAT123 cells were joined to human κ and γ1 C region genes in expression vectors containing dominant selectable markers, neo (Southern, P. J. & Berg, P. (1981) *J. Mol. Appl. Genet.* 1:327–341) and gpt (Mulligan, R. C. and Berg, P. (1981) *Proc. Natl. Acad. Sci. USA* 78:2072–2076), respectively. To construct the desired chimeric gene, the Hind III fragment of pV184ΔHneo.DNSV$_L$-hC$_\kappa$ (Oi, V. T. and Morrison, S. L. (1986) *Biotechniques* 4:214–221) containing the dansyl-specific $V_L$ gene was replaced with the 4.4 Kbp Hind III fragment containing the L chain gene of BAT123 derived from clone Vk123-23. The structure of the resulting plasmid pSV184ΔHneo.BAT123.VkhC$_\kappa$ is shown in FIG. 1A.

The chimeric H chain gene was constructed by replacing the EcoRI fragment in the pSV2ΔHgpt. DNSV$_H$.hc$_{\gamma 1}$ μlasmid containing the dansyl-specific $V_H$ gene with the 4.5-kbp EcoRI fragment containing the functionally rearranged BAT123 H chain gene derived from the phage clone VH123-E2. The structure of the resulting plasmid pSV2ΔHgpt.BAT123.V$_H$-hC$_{\gamma 1}$ is shown in FIG. 1B.

The L and H chain chimeric genes shown in FIG. 1 were used to transfect mouse myeloma cells. The myeloma cells chosen, Sp2/0, is a non-secretory cell line (Shulman, M., Wilde, C., and Kohler, G. (1978) *Nature* 276:269–270) that does not produce immunoglobulin molecules of its own. The calcium phosphate precipitation method (Graham and van der Eb (1973) *Virology* 52:456) was adopted to transfer the chimeric genes into Sp2/0 cells.

To facilitate the DNA transfection Sp2/0 cells were seeded at 5×10$^6$ cells per 100-mm Petri dish which had been previously treated with histone (Sigma Chemical Co., St. Louis, Mo.) and incubated for 16 hours at 31° C. Approximately 7.5×10$^7$ Sp2/0 cells were cotransfected with CsCl-ethidium bromide gradient purified pSV△184△Hneo.BAT123-VkhC$_\kappa$(150 μg) and pSV2△Hgpt.BAT123.V$_H$.hC$_{\gamma 1}$ (150 μg) using calcium phosphate precipitation method. Two days after transfection, cells were subcultured in microtiter plates at a density of 1×10$^5$ cells per well in culture medium containing 400 μg/ml G418 and 0.2 μg/ml mycophenolic acid. The frequency of transfectants resistant to both selection drugs was approximately 2×10$^{-5}$.

The stable transfectants (transfectoma) were screened for the production of secreted, functional chimeric antibodies by virtue of their affinity for purified HIV gp120, a distinct characteristic of BAT123. Purified gp120 was immobilized on microtiter plates, and allowed to react with culture supernatants from the transfectants. The antigen-antibody complexes were detected with alkaline phosphatase-conjugated antisera specific for human IgG. As shown in Table 1, 707 of the 1200 transfectants tested gave a positive signal in the ELISA, indicating that the intact chimeric antibody was secreted, and that this protein retrained the ability to bind HIV gp120. The untransfected parental cell line gave a negative result.

TABLE 1

Level of Secretion of Chimeric Antibody by Transfectomas

| Recipient Cell | Number Transfectoma Tested | Number Negative (−) | # Weakly Positive (+) | Number Positive (+) | Percent Positive |
|---|---|---|---|---|---|
| SP2/0 | 1200 | 493 | 511 | 196 | 59 |

Transfectomas were scored based on their OD in ELISA. "Negative" is defined as OD of 0.0 to 0.1, "Weakly positive" denotes 0.1 to 0.2 and "positive" indicates 0.2–3.0.

Production of Chimeric Antibody from Transfectoma Cell Lines

Seventeen transfectoma lines exhibiting OD greater than 1.0 in ELISA were selected and the chimeric antibody producing cells were purified by single cell cloning technique from which twelve stable cell lines were established. These transfectoma cell lines were then tested for stability of chimeric antibody production in the absence of selection drugs G418 and mycophenolic acid. The cells were cultured in the medium with stepwise reduction in the two selection drugs at 2-week intervals which resulted, in the complete elimination of the drugs. During each reduction of drugs the production of the chimeric antibody in these cell lines were monitored by ELISA. Three of these cell lines lost their ability to secrete chimeric antibody upon removal of selection pressure. The remaining 9 cells lines remain stable in the production of chimeric antibody at 5 weeks after complete elimination of selection drugs in the culture medium.

To estimate the level of chimeric antibody production and to prepare the antibody for further characterization, transfectoma line CACl-51-4 was expanded and grown in tissue culture medium. Approximately 600 ml of culture medium was collected and from which 14.4 mg (estimated by BCA protein assay, Pierce, Rockford, Ill.) of the chimeric antibody was purified by utilizing r-protein A-Sepharose affinity column (Repligen Corporation, Cambridge, Mass). The IgG concentration in the culture supernatant of this transfectoma cell line was therefore estimated to be 24 µg/ml, a level somewhat higher than the level produced by BAT123 hybridoma cells (20 µg/ml).

Biochemical Analysis of Chimeric Antibody

Purified chimeric immunoglobulin was used to characterize the biochemical/immunological properties of the chimeric antibody.

A) Isoelectric points

Figure 2:
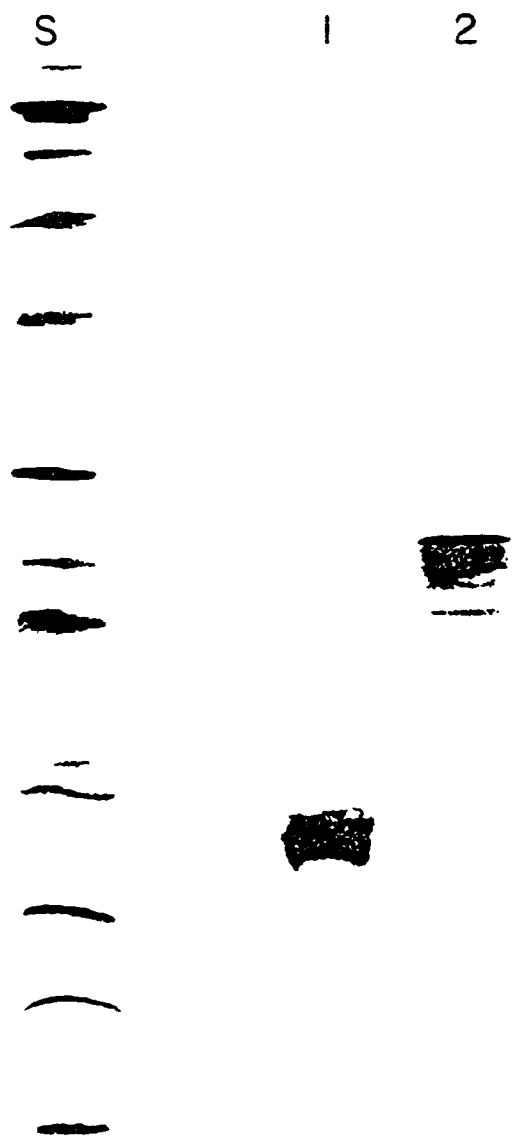
FIG. 2 shows isolelectric focusing patterns of the chimeric HIV-neutralizing antibody (lane 2) and the murine monoclonal antibody BAT123 (lane 1). S represents the pH calibration standard proteins with pI values of (from cathode (top) to anode (bottom)): 8.65, 8.45, 8.15, 7.35, 6.85, 6.55, 5.85, 5.20, 4.55, and 3.50.

The pattern of isoelectric focusing (IEF) gel of the purified chimeric antibody along with that of BAT123 is shown in FIG. 2. The IEF pattern was obtained by application of purified antibody samples onto Pharmacia's Phast System TH and IEF was carried out according to the procedure recommended by the manufacturer. The IEF pattern indicated that the chimeric antibody contained two major species of molecules with pI in the range of pH 6.8–7.2 whereas the corresponding molecules of BAT123 exhibited pI in the range of pH 5.6 to 5.8. The replacement of constant regions of the immunoglobulin molecule from mouse to human therefore greatly altered the composition of the antibody which is reflected in the IEF pattern.

Figure 3:
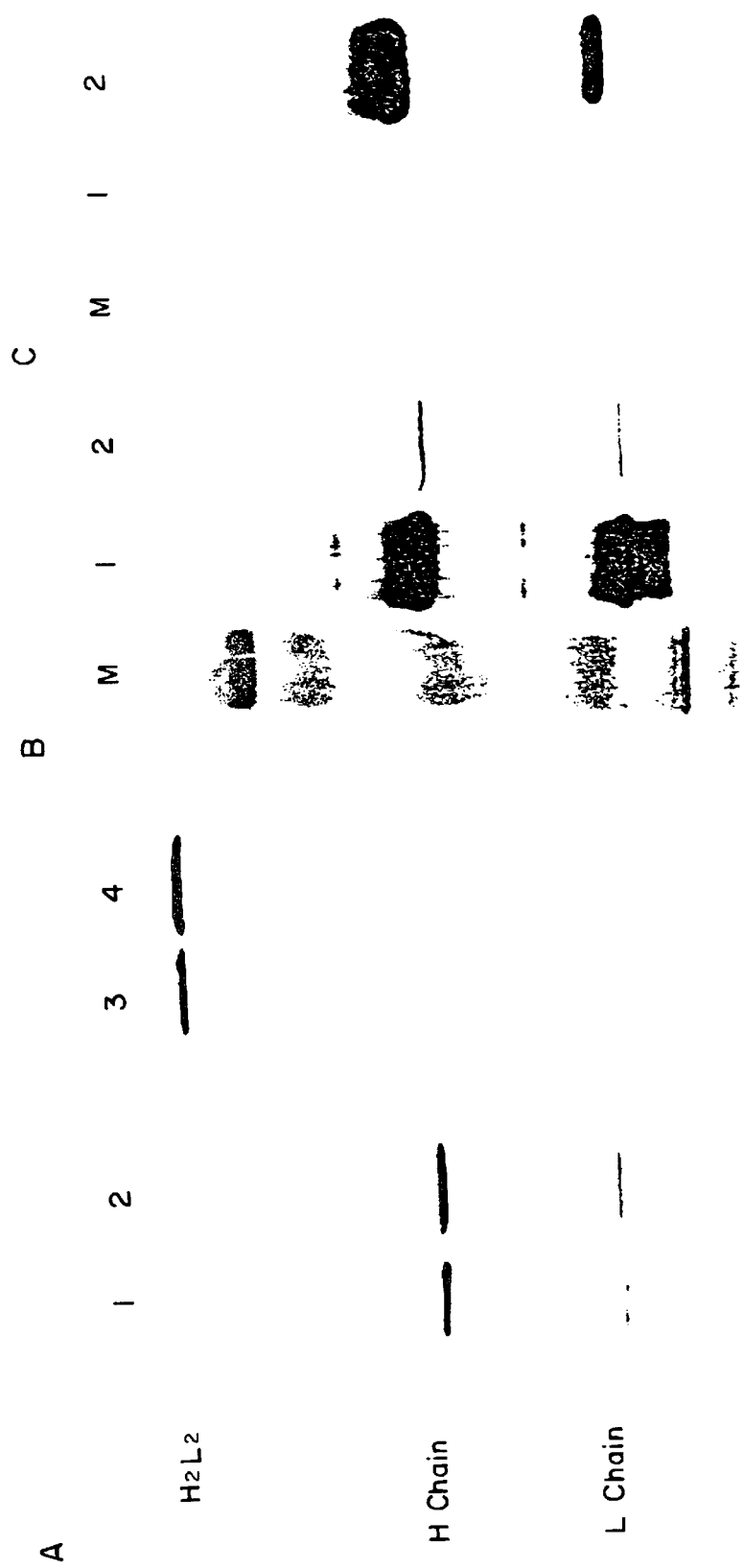
FIG. 3 shows electrophoretic analysis of the chimeric immunoglobulin. (A) Immunoglobulins purified by r-protein A affinity chromatography were analyzed by electrophoresis on a 10% SDS-poly-acrylamide gel with or without reducing the disulfide bonds. Lane 1, BAT123, reduced; lane 2, chimeric antibody, reduced; lane 3, BAT123, un-reduced; lane 4, chimeric antibody, reduced. (B) Western blot analysis of the immunoreactivity of the immunoglobulin to anti-mouse antibody. Purified immunoglobulin (2 μg) were resolved in 10% SDS-PAGE under reducing conditions, electro-transblotted onto nitrocellulose membrane filter and reacted with anti-mouse antibody. Lane 1, BAT123, lane 2, chimeric antibody. (C) Duplicate transblotted membrane from (B) was reacted with anti-human antibody. Lane 1, BAT123; lane 2, chimeric antibody.

B) Reactivity of the Chimeric Antibody to anti-mouse as well as anti-human antisera When the chimeric antibody was subjected to a 10% SDS-polyacrylamide gel electrophoresis under reducing conditions (Laemmli, U.K. (1970) *Nature* 227;680–685) two bands were observed (FIG. 3A, Lane 2). Protein band of molecular weight of 53,000 daltons corresponds to the chimeric heavy chains, and exhibits a close similarity in size to the heavy chains of BAT123 immunoglobulin (FIG. 3A, Lane 1), The protein band with the size of approximately 23,000 dalton denotes the light chains of antibodies. The slightly slower mobility observed for chimeric light chains is also seen in other chimeric antibody and may not necessarily be attributed to the larger size of human light chain a constant region ($hC_\kappa$) than the murine counterpart. The fully assembled $H_2 L_2$ molecule of the chimeric antibody shows identical mobility to that of BAT123 (mw 146,000 dalton) when the immunoglobulins were resolved in the 10% SDS-PAGE under non-reducing conditions (FIG. 3A, Lanes 3 & 4).

To test whether the chimeric antibody indeed incorporated the constant regions of human immunoglobulin, 2 µg of the chimeric antibody and BAT 123 were electroblotted onto a nitrocellulose membrane (100 volts, 1 hour in a transblot buffer consisting of 25 mH Tris-Hcl, 192 mM glycine, 20% (v/v) methanol, pH 8.3) after the proteins were resolved in 10% SDS-PAGE under reducing conditions in a BioRad Mini-Protein II Dual Slab Cell apparatus. One of the replica membrane filters was reacted with biotinylated anti-mouse antibody (Vector Laboratory, Burlingame, Calif.) whereas the other filter was reacted with biotinylated anti-human antibody in Blotto buffer consisting of 5% non-fat dry milk in phosphate buffered saline (PBS). After 1 hour incubation at 37° C., the membrane filters were washed with 2 changes of PBS+0.1% Tween 20 (PBST) and both membranes were reacted with horseradish peroxidase-avidin conjugate in Blotto at room temperature for 30 minutes. After final washes with PBST the reactive protein bands were visualized by color development using 4-chloro-1-naphthol (4-CN) and hydrogen peroxide. As shown in FIG. 3B, BAT123 immunoglobulin was extensively reactive with antimouse antiserum whereas chimeric antibody is only barely reactive to the same serum. On the other hand, chimeric antibody reacted strongly with anti-human antiserum whereas BAT123 did not show appreciable reactivity to the antiserum (FIG. 3C). This result demonstrated that portions of the chimeric antibody molecule was indeed derived from human immunoglobulin.

C) The IgG Subclass of the Chimeric Antibody

Figure 4:
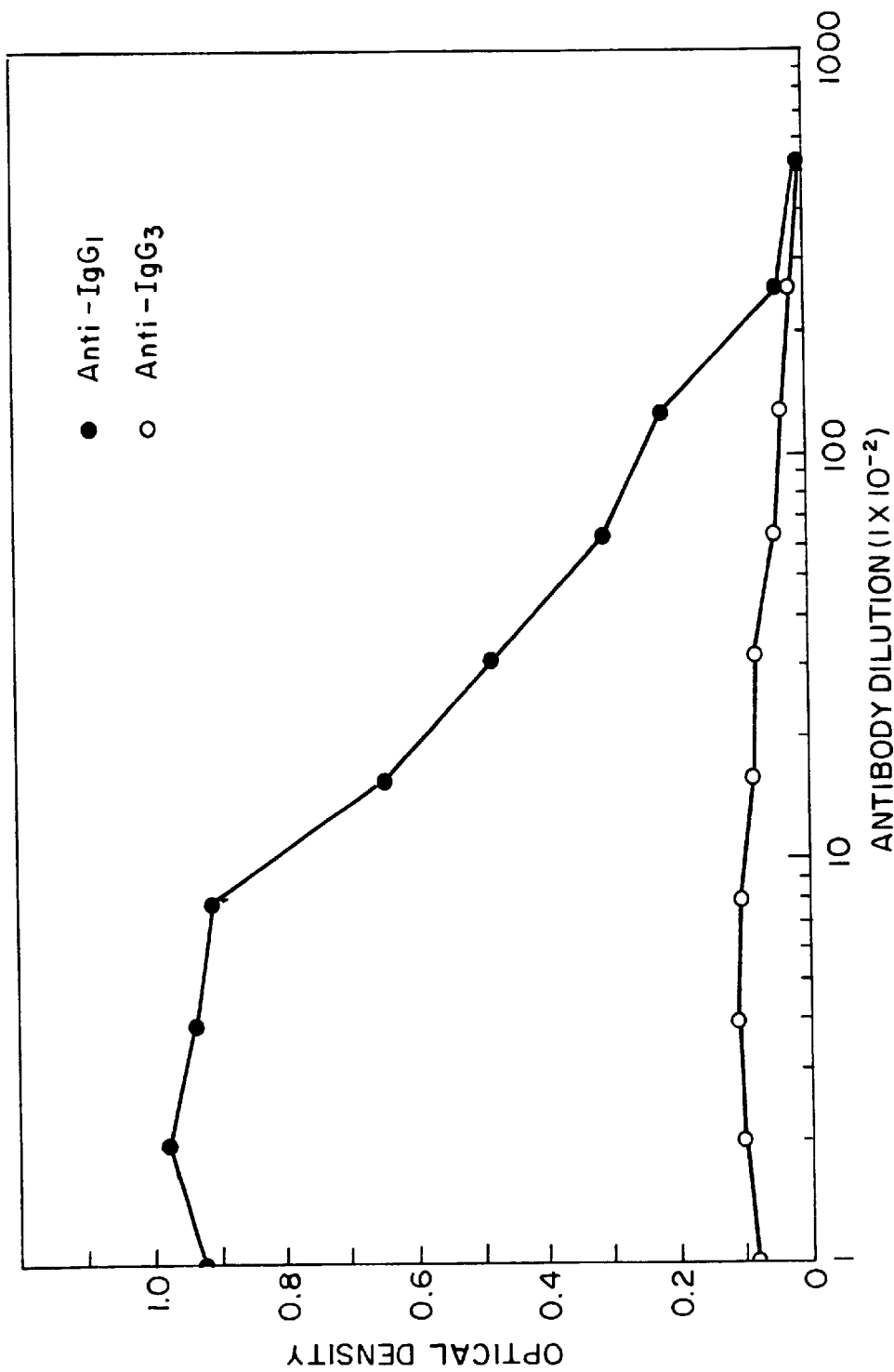
FIG. 4 shows the IgG subclass of the chimeric antibody as assayed by its reactivity to the anti-sera in ELISA. Anti-sera used were (●) anti-human IgG1, (○) anti-human IgG3.

The heavy chain chimeric gene was constructed by splicing the $V_H$ gene of BAT123 into the coding sequence of human $C_{\gamma 1}$ region. The resulting chimeric antibody was therefore expected to be of IgG1 subclass. To confirm the isotype of the expressed constructed chimeric antibody the following experiment was conducted. Mouse anti-human IgG1 and IgG3 anti-sera (Fisher Biotech) were separately coated onto microtiter wells in series of 2-fold dilutions. Chimeric antibody at 20 µg/ml was added to these wells and incubated at 37° C. for 1 hour. After washes with PBST the complexes were detected by incubation with goat anti-human-horseradish peroxidase conjugate (Vector) with a subsequent color development. The result (shown in FIG. 4) clearly demonstrated that chimeric antibody is of IgG1 subclass.

D) Antigen Specificity of the Chimeric Antibody

Figure 5:
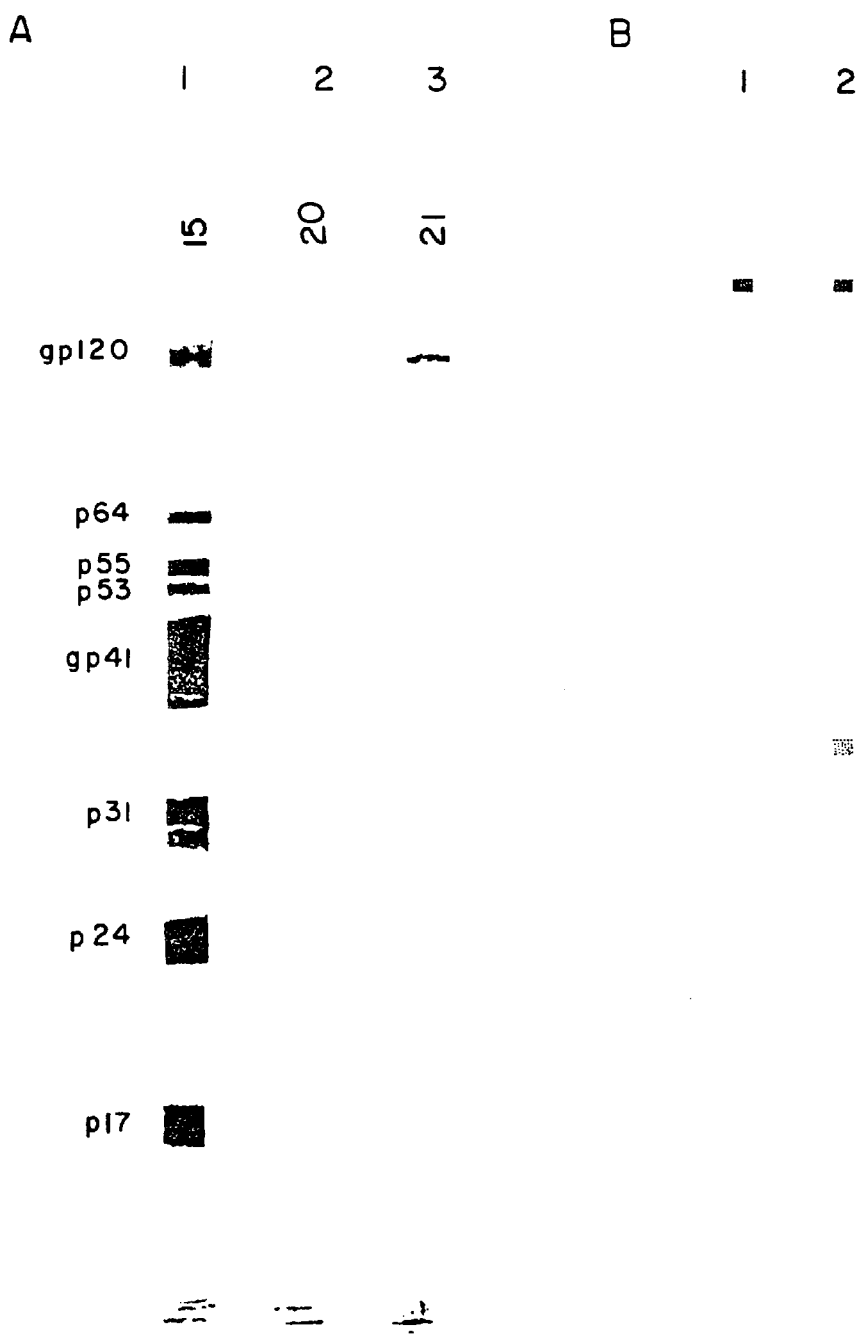
FIG. 5 shows Western blot analysis of the antigen specificity of the chimeric antibody. (A) Immunoreactivity of the immunoglobulins to HIV-1 antigens which were resolved in SDS-PAGE and trans-blotted onto nitrocellulose membrane filters. Strip 1, an AIDS patient serum (1:200 dilution), strip 2, BAT123 (1 μg/ml); strip 3, chimeric antibody (1 μg/ml). (B) Reactivity of the antibody to the synthetic oligopeptides representing potential antigenic determinants (epitopes) of HIV-gp120 which were blotted on nitrocellulose membrane filter. Strip 1, BAT123; strip 2, chimeric antibody.

The amino acid residues within an immunoglobulin molecule that are directly involved in the formation of the antigen binding site are generally believed to be in the complementarity determining region (CDR) which reside in the variable domain (V) of the immunoglobulin. To determine if the chimeric antibody retained the antigen specificity of the parent antibody the following experiments were performed. In the first experiment the chimeric antibody was allowed to react with a commercially available immunoblot strip (gift of Dr. Robert Ting, Biotech Research Labs) that contains all antigens of purified HIV resolved in SDS-PAGE with a subsequent electrotransblot on to nitrocellulose membrane filters. The reaction was carried out at room temperature for 16 hours in blotto buffer. The reactive complexes were then detected by incubations first with biotinylated-anti-human antisera (Vector) followed by avidin-horseradish peroxidase with washes in between each incubation step and finally visualized by color development with the enzyme substrates 4-CN and hydrogen peroxide. The result was shown in FIG. 5A. The antigen band that reacted with the chimeric antibody (lane 3) was identical to the one detected by BAT123 antibody in a parallel reaction (lane 2) and corresponded to the viral envelope glycoprotein gp120 in a viral antigen profile displayed by reaction with a reference serum from patient with AIDS. This result showed that the chimeric antibody retained the antigen specificity of BAT123 to bind HIV-gp120.

To further test whether the chimeric antibody recognizes the same antigenic determinant (epitope) within gp120 as does BAT123, the antibody was allowed to react with a membrane strip containing a series of 32 overlapping oligopeptides that represent the potential antigenic determinants in gp120 (gift of S. Petteway, Du Pont). The incubation procedure was essentially the same as that for the immunoblot strip of viral antigens. The result (shown in FIG. 5B) indicates that the chimeric antibody binds to the same oligopeptide as does BAT123 which has the amino acid sequence of Arg•Ile•Gln•Arg•Gly•Pro•Gly•Arg•Ala•Phe•Val•Thr•Ile•Gly•Lys The antigen specificity of the murine antibody BAT123 was therefore well preserved upon conversion into a mouse/human chimeric antibody.

Biological Activity of the Chimeric Antibody

A) Neutralization of HIV-1 infection to H9 Cells by Chimeric Antibodies

The ability of the chimeric antibodies to neutralize the HIV-1 infection to H9 cells was measured using the similar procedure described earlier (U.S. patent application Ser. No. 137,861 filed Dec. 24, 1987, which is a continuation-in-part of U.S. application Ser. No. 057,445, filed May 29, 1987). The virus used was prepared from culture supernatants of HTLV-IIIB-infected H9 cells. 40 ml of cell-free supernatant was centrifuged at 35,000×g for 3 hours. The pellet was resuspended in 3 ml of growth medium. The titer of the virus was measured by infecting H9 cells with the viral stock in ten-fold serial dilutions. The $TCID_{50}$ of the viral stock was determined as the infective dose at which half of the number of the minicultures was infected.

In the neutralization assay, an infectivity dose equivalent to 20 times of the $TCID_{50}$ was used. 50 μl of 60 $TCID_{50}$ of the viral stock was pre incubated with 50 μl the antibodies tested in a microculture well of a 96-well plate. The antibodies tested were the chimeric antibody CAG1-51-4, the murine monoclonal antibody BAT123 and a murine monoclonal antibody to human chorionic gonadotropin (anti-hCG). In the control, 50 μl of growth medium without any antibodies was used. The mixtures were kept at 37° C. in a 5% $CO_2$ incubator for 1 hour. The final concentration of the antibody was 100, 50, 25, 12.5 and 6.25 μg/ml. Each concentration of the tested antibodies was performed in triplicate. At the end of the incubation, 50 μl of 4×10$^6$/ml. H9 cells was added. The H9 cells were harvested in phase and pre-incubated for 1 hour at 37° C. with 2 μg/ml polybrene in the RPMI-1640 growth medium containing 15% heat-inactivated fetal bovine serum before being added to the mixture. At the end of the incubation, the cells. in each microculture wells were resuspended, 40 μl of the-cell suspension was added to 200 μl of fresh growth medium in the corresponding wells of another microculture plates. The microculture plates were kept at 37° C. in 5% $CO_2$ in an incubator. On day 3, day 5, day 7, day 9, day 11, and day 14 150 μl of cell suspension from each microculture was removed and placed into a U-bottomed well of another 96-well plate. The plate was centrifuged at 200×g for 5 minutes. The supernatants were collected for HIV-1 viral antigen capture assays: The wells were fed with 150μl fresh growth medium.

Figure 6:
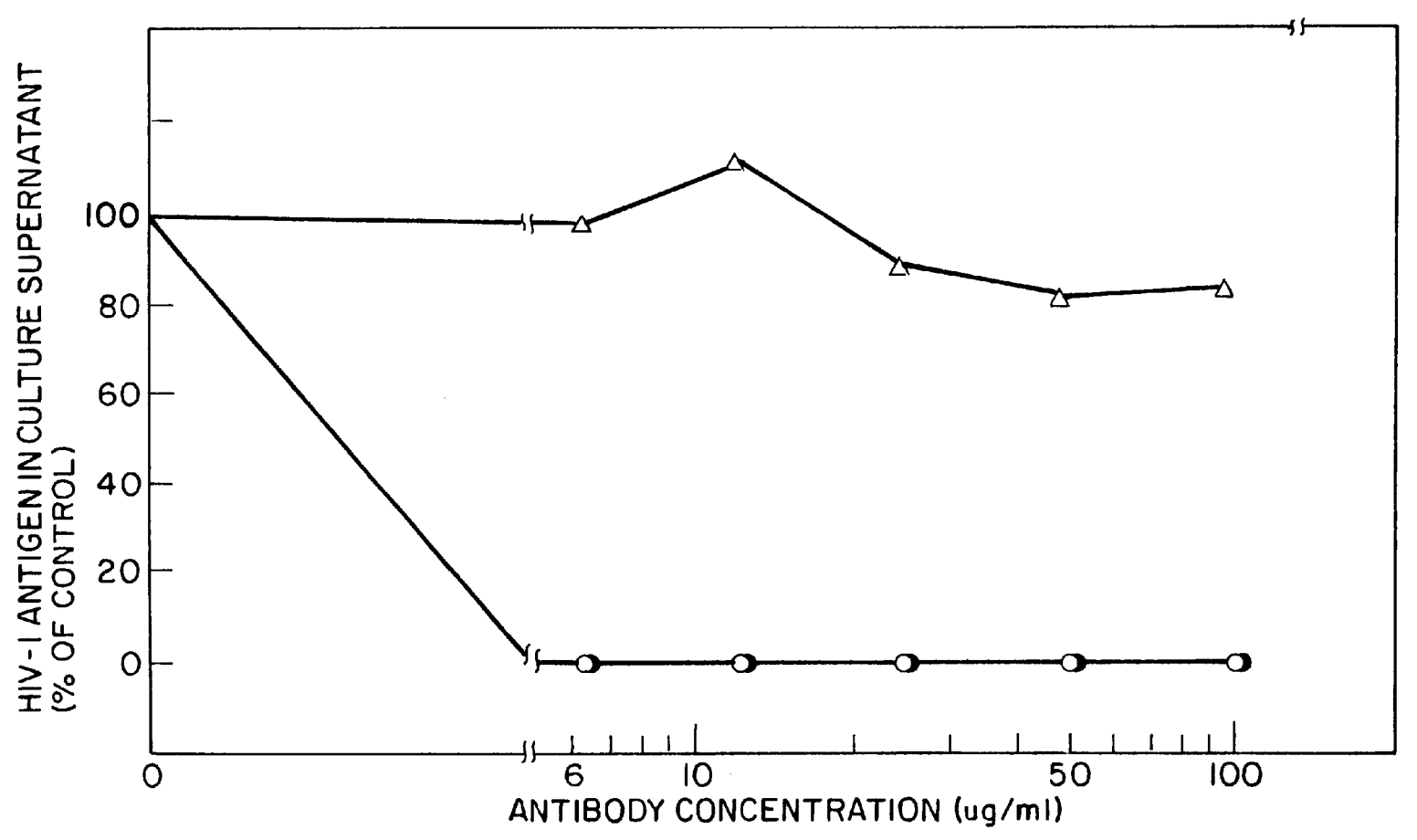

In the antigen capture assay, the HIV-1 specific antigens in the cell-free supernatant were measured by virtue of their affinity for the immuno globulins from patients with AIDS. One hundred μl of diluted purified AIDS patient immunoglobulin (1:2000, approximately 5 μg/ml) was added to each, well of a Cobind plate and incubated for 2 hours at 37° C. Then the wells were rinsed two times with 200 μl of phosphate-buffered saline (PBS). The wells were blocked with 220 μl of It bovine serum albumin (BSA) in PBS for 1 hour at 37° C. Then it was rinsed three times with PBST (PBS containing 0.1% Tween 20). The wells were then emptied. 50 μl of the test samples (undiluted or in appropriate dilution) together with 50 μl of PBSTB (PBS containing 1% BSA and 0.1% Tween 20) were added to the well. The negative control contained 50 μl of the growth medium. The plate was incubated for 1 hour at 37° C. Then it was rinsed three times with PBST. 100 μl of diluted peroxidase conjugated AIDS patients immunoglobulins was added to each well for 1 hour at room temperature. The plate was then rinsed three times with PBST. 100 μl of a substrate solution (containing 20 mM sodium acetate buffer pH 6.0, 0.001% 3,3',5,5' tetramethylbenzidine and 0.001% hydrogen peroxide) was added to each well and incubated for 30 minutes at room temperature. Then 50 μl of 2M $H_2SO_4$ was added to each well to stop the reaction. The absorbance was read at 490 nm. The readings from the triplicate were averaged and compared between the control and the test antibody for the percent of inhibition when neutralizing antibodies were added. The results (FIG. 6) showed that at all dilutions the chimeric antibody completely neutralized the HIV-1 infection to H9 cells at a 14-day assay. This neutralizing activity was identical to that of the parent murine antibody BAT123. A control murine antibody (anti-hCG) and the growth medium did not exhibit any inhibitory activity.

B) Inhibition of Syncytium Formation by Chimeric Antibody

The HIV-neutralizing activity of the chimeric antibody was also assessed by its ability to inhibit syncytium formation. The effects of chimeric antibody on HIV-1 transmission via cell fusion were studied using HIV-1 infected H9 cells and CD4-expressing HeLa cells.(HeLa-CD4+), which fuse upon contact and form syncytia in culture. HeLa is a human carcinoma cell line. HeLa-$CD_4$+ contains in its genome, CD4 encoding DNA introduced by transfection and thus, it expresses CD4 antigen on its cell surface. The HeLa-$CD_4$+ cell line was a gift from David. D. Ho (University of California, Los Angeles). A culture of HeLa-$CD_4$+ cells were plated onto wells of 96-well microculture plates at 20,000 cells per well. The plates were incubated for 36 hours and by this time, the monolayer epithelial cells were almost confluent. When 1×10$^4$ infected H9 cells were added to the confluent HeLa-CD4+ cells, the cells formed contacts and fused, and by 18 hours multinucleated giant cells (syncytia) formed. Those syncytia with more than five nuclei could be easily identified and enumerated, thus providing quantitative measurements of syncytium formation. When the effects of chimeric antibodies on syncytium formation were studied, antibodies at different concentrations were mixed with infected H9 cells and added to the HeLa-CD4+ cells. The final total volume of the culture medium per well was 200 μl. At the end of 18 hours incubation at 37° C., the wells were washed with PBS, fixed with methanol, air-dried, and stained with methylene blue. The cells were examined at 100X magnification and the number of syncytia (of more than 5 nuclei) were determined in four randomly chosen fields and averaged. As shown in Table 2, the chimeric antibody CAG1-51-4 gave 89.1%, 65.7% , and 58.6% reduction in the number of syncytia formed between H9 cells and Hela-$CD_4$+cells at levels of 20 μg/ml, 10 μg/ml, and 5 μg/ml, respectively. This effect is essentially identical to that caused by BAT123 and it indicates that the chimeric antibodies retained the activity to inhibit the fusion between the HIV-infected cells and uninfected cells, one of the major routes for HIV transmission The control murine antibody anti-hCG gave no effect on the syncytium formation.

TABLE 2

Inhibition of Syncytium Formation Between HIV-1 Infected H9 Cells and HeLa-CD4+ Cells by Chimeric Antibody

| Antibody Tested | | Number of Syncytia* per field | Percent Inhibition |
| --- | --- | --- | --- |
| Control (no antibody) | | 37 ± 2.6** | |
| BAT123 | 20 μg/ml | 3.67 ± 2.1 | 90.0 |
| | 10 μg/ml | 11.3 ± 2.1 | 69.5 |
| | 5 μg/ml | 18.0 ± 2 | 51.4 |

TABLE 2-continued

Inhibition of Syncytium Formation Between HIV-1 Infected H9 Cells and HeLa-CD4+ Cells by Chimeric Antibody

| Antibody Tested | | Number of Syncytia* per field | Percent Inhibition |
|---|---|---|---|
| CAG1-51-4 | 20 μg/ml | 4 ± 3 | 89.1 |
| | 10 μg/ml | 12.7 ± 4 | 65.7 |
| | 5 μg/ml | 15.3 ± 1.2 | 58.6 |
| α-hCG | 20 μg/ml | 35.0 ± 5 | — |
| | 10 μg/ml | 33.7 ± 7 | — |
| | 5 μg/ml | 32.0 ± 5 | — |

*No. of syncytia from 5 randonly selected microscopical field at a magnification of 100x.
**Results expressed in x ± S.D., n = 3

EXAMPLE I

Preparation of the Hybridomas and Monoclonal Antibodies a) Preparation of Virus In order to maintain a supply of inactivated HIV-1, a virus stock was prepared as follows. The H9 clones of the HT cell line (which is described by M. Robert-Guroff et al. in *Nature* 316:72–74, supra) were maintained in culture. These H9 cells were infected with HIV-1 (HTLV III$_B$), which was a gift from Dr. R. Ting, Biotech Research Laboratory, Rockville, Md. Maintaining the infected H9 cells in culture permits the cells to reproduce and to continuously synthesize a supply of HIV-1. The H9 cells were cultured in a growth medium of 20% FBS (heat-inactivated) RPMI 1640, supplemented with 5 mM L-glutamine, 5 mM HEPES, 50 units/ml penicillin and 50 mg/ml streptomycin.

Purified HIV-1 was obtained by first centrifuging the cell culture at 1000 g for ten minutes to remove the cells and debris. The supernatant was then centrifuged at 90,000 g for one hour. The virus pellet was resuspended in minimal volume of phosphate buffered saline pH 7.4 and loaded onto a centrifuge tube with a preformed sucrose gradient (20%–60%). The sample was then centrifuged at 100,000 g for sixteen hours. The virus was collected at the gradient of 38%. The virus was then aliquoted and frozen at −80° C. after the protein, content was measured.

b) Immunization Procedure

Male Balb/c mice were used for the immunization. Each mouse received 100 micrograms of inactivated HIV-1. The inactivation of the virus was performed according to NIH CDC approved protocol, by UV irradiation and addition of a detergent, Nonidet P-40 (0.1%). A volume of suspension containing 100 micrograms of virus per mouse was suspended in 200 microliters phosphate buffered saline (PBS), and emulsified with equal volumes of complete Freund's adjuvant.

Each mouse was immunized subcutaneously with 100 micrograms of the emulsified virus. The mice were injected at sites with high concentrations of lymph nodes, for example, the underside of the intersection of the limbs and the trunk. One month later the mice received subcutaneous booster injections at the same sites with the same quantity of virus. The boosters were prepared essentially in the same manner as was the first injection, except that for the boosters the emulsification was done in incomplete Fruend's adjuvant.

One month later, each mouse was reimmunized subcutaneously with 100 micrograms of virus suspended in PBS. Each mouse was injected sub-cutaneously at the intersection of each limb with the trunk, and intraperitoneally. Three days after the last injection, the mice were sacrificed and their spleens were removed. The spleen cells were then fused with myeloma cells by the following procedure.

c) Fusion

Suspensions containing a five-to-one ratio of spleen cells to myeloma cells were prepared. The myeloma cells chosen were NS-1. The NS-1 cells were conditioned to have a doubling time about every seventeen hours. They were used for fusion when in the log phase. The NS-1 cells were subcultured in bacteriological plates (100 mm) at a concentration of $6 \times 10^4$ cells/ml in 10 ml of Dulbecco's Modified Eagle's Medium (DMEM) containing 5% Fetal Bovine Serum (FBS), 100 units/ml of penicillin and 100 micrograms/ml of streptomycin. The medium was changed every three days. Alternatively, the cells were subcultured at $1.54 \times 10^5$ cells/ml in 10 ml of the same medium, and the medium was changed every two days.

The spleen cells were prepared by placing the spleen on a bacteriological plate (100 mm) and injecting 20 ml of calcium magnesium free PBS (CMF-PBS) into both ends of the spleen to flush out the spleen cells. The flushed spleen cells were then transferred to a 50 ml centrifuge tube.

The spleen cells were centrifuged at 400 g for five minutes, and then suspended in 5 ml of 0.83% NH$_4$Cl (0.155 M) for ten minutes at room temperature to lyse the erythrocytes. 5 ml of CMF-PBS was added to the tube to stop the lysis. The cells were then pelleted, and resuspended in 10 ml of CMF-PHS.

The concentration of lymphocytes was determined by adding 40 microliters of cell suspension to 10 ml of saline together with 3 drops of Zap-oglobin™. The number of lymphocytes was counted with a hemacytometer and from this value the concentration of cells was determined. The concentration was then multiplied by the dilution factor of 250 to yield the actual concentration of cells in the suspension.

The NS-1 cells were transferred from five of the bacteriological plates (100 mm') to a 50 ml centrifuge tube. The cell concentration was determined using the counting technique described above. $5 \times 10^7$ of the NS-1 cells were then, suspended in 10 ml of CMF-PBS and mixed with $2.5 \times 10^8$ spleen cells in a 50 ml centrifuge tube.

The cells were spun down and washed once with 10 ml of CMF-PBS. The supernatant was aspirated as much as possible with a glass Pasteur pipette. The tube was gently tapped to free the cell pellet.

Prior to preparing the cells, a fusion mixture had been prepared as follows. 5 g of polyethylene glycol 1450 (purchased from Kodak) had been mixed with 5 ml of CMF-PBS and 0.5 ml of DMSO. This mixture had then been warmed to 56° C. to melt it, titrated to a final pH of 7.0, and,filtered through a 0.22 micron Millipore filter in order to sterilize it. 1.0 ml aliquots had been added to Cryotubes, and these had been stared at −70° C.

To prepare the fusion mixture for use, one of the aliquots in the Cryotubes was melted by heating it to 37° C. Separately, a tube containing 1-ml of DMEM (without serum) was heated to 37° C.

The 1.0 ml aliquot of polyethylene glycol fusion mixture was added to the cell suspension and the suspension was mixed well. Forty-five seconds after the polyethylene glycol fusion mixture had been added, 2.0 ml of the pre-heated DMEM (without serum) was added dropwise with mixing.

The remaining 8 ml of the pre-heated DMEM (without serum) was then added. The cells were left at room temperature for 10 minutes.

2.0 ml of FBS was added to the suspension and the suspensions were mixed well. The combination of the FBS and the DMB-PBS can help to prevent adherence of cells to the test tube walls. The suspensions were then centrifuged at 400 g for four minutes.

After having been spun down, the cells were suspended in 116 ml of a modified medium, supplemented with 5% FBS, 100 units/ml of penicillin, 100 micrograms/ml of streptomycin, and Littlefield's hypoxanthine, aminopterin and thymidine (HAT).

The concentration of the cell suspension was adjusted to $3.3 \times 10^5$ of the spleen cells per 200 microliters of suspension. 200 microliter aliquots of suspension were then distributed to each well of a 96 well microtiter plate. After seventeen such plates were prepared, the plates were transferred to an incubator and maintained at 37° C. in 5% $CO_2$.

The cells were grown for seven days in the plates, then the growth medium was withdrawn and new medium was added. Four days after that, the medium was again changed. Four days later, an enzyme linked immunosorbent assay (ELISA) was performed on the antibodies in the wells to determine which would bind the gp 120 protein of HIV-1. The ELISA was carried out as follows.

d) ELISA Procedure

Purified gp 120 protein was prepared as described in W. G. Robey, "Prospect for Prevention of Human Immunodeficiency Virus Infection: Purified 120-kD Envelope Glycoprotein Induces Neutralizing Antibody". *Proc. Natl. Acad. Sci. USA* 83:7023–27 (1986). 50 microliters of a gp 120 suspension (at a concentration of 0.1 to 1.0 micrograms/ml) was added to wells of 96-well Immulon I plates with a twelve-channel pipette. The plates were covered and incubated for eighteen hours at 4° C., in order to allow the protein to bind to the plate.

The liquid contents of the plates were then emptied, and 200 microliters of 0.1 M $NH_4Cl$ was added to each well in order to saturate any remaining binding sites on the plates. The NH4Cl solution was left in the wells for thirty minutes at room temperature.

The NH 4Cl solution was then removed and the wells were washed three times with PBS and 0.05% Tween 20. Some of the PBS/0.05% Tween 20 solution was left in the wells until the antibody suspension described below was added.

50 microliters of the cell fusion supernatant from each well of the seventeen 96 well plates was added to each of the wells on the Immulon I plates, and incubated for one hour. Following incubation, the plates were rinsed three times with PBS/0.05% Tween 20 in order to remove any unbound antibody.

The cell fusion supernatant will contain the antibody which is produced by the various hybridomas in the 96 well plates. The antibody which is specific to gp 120 will bind thereto. Inasmuch as the gp 120 is bound to the Immunlon I plate, the antibody specific to gp 120 will also become bound to the plate.

The next stage is to add the marker which will indicate the amount of bound antibody in each well. The marker chosen was horseradish peroxidase. This marker. was conjugated with goat anti-mouse IgG to yield peroxidase-conjugated goat anti-mouse IgG. The goat anti-mouse IgG will bind to any mouse monoclonal antibody which is bound to the palte. The peroxidase marker can then be activated to indicate the quantity of bound antibody by an exzyme reaction.

The marker was added by adding to each well 100 microliters of the peroxidase-conjugated goat anti-mouse IgG diluted at 1:1000 in PBS/0.05% Tween 20 and 1% BSA. The plates were incubated for one hour at room temperature. Thereafter, the plates were washed three times with PBS/0.05% Tween 20 to remove any unbound goat anti-mouse IgG conjugate.

The next step is to activate the peroxidase marker which is conjugated to the goat anti-mouse IgG. This is done by adding 200 microliters of 3', 3', 5', 5' tetramethyl benzidine substrate solution to each well, and incubating at room temperature for 30 minutes. The color reaction is stopped by adding 50 microliters of 2.0 M $H_2SO_4$.

The intensity of color was determined with an ELISA reader at 450 nm. The amount of antibody specific to gp 120 is proportional to the intensity of the color.

It was found that there were approximately 200 wells in the 96 well microtiter plates which produced antibodies which bound to gp 120 to at least some extent. Of these 200 wells the 39 which produced antibody showing the highest color intensity were selected for another screening step.

e) Immunofluorescence Assay Using Live T-Cells

An immunofluorescence assay was performed to determine whether any of the antibodies which were reactive with gp 120 in the ELISA would bind specifically to live HIV-1 infected H9 cells. The H9 cell line is permissive to, persistent infection by HIV-1. This cell line was obtained from the American Type culture Collection in Rockville, Md. Antibody which binds to -infected cells, but not uninfected cells, is probably selective to a domain of the HIV-1 envelope protein on the extra-cellular side of the cell membrane. The immuno-fluorescence assay helps to select those gp 120 reactive antibodies which have a high potential to recognize the neutralization epitopes on the HIV-1 virion, and to inhibit syncytium formation by infected T-cells.

Cultures of infected H9 cells were maintained as described above under the heading "Preparation of Virus". The procedure by which the assay was performed is described below.

(i) Assay Procedure 50 microliter aliquots of infected H9 cell suspension at a concentration of $5 \times 10^6$ cells/ml was added to each of thirty-nine 1.5 ml microfuge tubes. 50 microliter aliquots of the supernatant from the 39 wells containing the ELISA positive clones was then added to each tube. The antibodies in the supernatant which react with H9 cells will bind to any H9 cells which are in the tube.

The tubes were then incubated for thirty minutes at room temperature. After incubation, the tubes were spun, the supernatant was withdrawn, and the cells were washed three times with a mixture of RPMI 1640, containing 2% fetal calf serum and 0.1% sodium azide. The tubes were then tapped to loosen the cell pellet.

10 microliters of labeled antibody, goat anti-mouse IgG conjugated with fluorescein isothiocyanate (FITC), was added to each test tube at a dilution of 1 to 200. This labeled antibody will bind to any monoclonal antibodies which have attached to HIV-1 infected H9 cells and provide a means for identifying these monoclonal antibodies.

The tubes were again incubated for thirty minutes at room temperature. The tubes were centrifuged, and the cells were washed with the same medium as before. The cells were then resuspended in PHS, placed onto individual slides and cover-slipped. The cells were viewed with a fluorescence microscope.

To determine which of the thirty-nine selected wells contained antibodies which specifically bound to HIV-1 infected H9 cells, an essentially identical procedure as described above was performed, using uninfected H9 cells instead to control.

(ii) Results

Seven of the thirty-nine wells tested contained clones which produced monoclonal antibodies binding to live infected H9 cells but not to-uninfected H9 cells. That is, when using antibodies from these seven wells the infected cells fluoresced, but the uninfected cells did not.

Cells and antibodies from the seven wells which contained immunofluorescence positive clones were collected. These hybridomas and antibodies have been deposited at the American Type Culture Collection in Rockville, Md., and are available for inspection by the Patent and Trademark Office during the pendency of this application.

f) Single Cell Cloning

Cell suspensions from each of the thirty-nine ELISA positive wells were expanded in the wells of a twenty-four well plate. After five days of growth in the twenty-four well plate, the cell suspension from the seven wells tested immunoreactive to infected H9 cells which were diluted to thirty, fifty and one hundred cells per milliliter. 0.1 ml of the diluted cell suspensions (containing an average of three, five and ten clones, respectively) was placed into the wells of a nine-six well plate. The wells had previously been coated with histone.

After each cell grew up to become a colony, the cells were checked under a microscope. The cells of each colony did not move about and form satellite colonies. The single-cell clone from each of the seven clonings showing strongest reactivities in ELISA and immunofluorescence was chosen and expanded in culture.

g) Sodium Dodecyl-Sulfate Polyacrylamide Gel Electrophoresis (SDS-PAGE) and Western Blot Procedure In Western blot analysis, the virus is solubilized into its component proteins. The clones which produce monoclonal antibodies binding to the exterior envelope protein of HIV-1 (gp 120) are the ones which are desired. The procedure is described below.

30 micrograms of HIV-1 was solubilized by heating it in a sample buffer (which contained 2% SDS and 5% beta-mercaptoethanol) at 100° C. for five minutes. It was then loaded onto a 12% slab polyacrylamide gels 1.5 mm thick. The gel was run at constant voltage of 35 mV for 8 hours at room temperature. The procedure was described in "Procedure for Preparation of Gels for Western Blot Detection of HTLV-III Antibodies", published by Biotech Research Laboratories, Inc., Rockville, Md. The protein bands were transferred onto nitrocellulose paper by setting the power at 30 volts (about 0.1 A) and running for 16 hours at room temperature. The next morning, the voltage was increased to 60 volts (about 0.2 A) and the transfer was run for 1–2 hours to maximize the transfer of gp 120 and gp 160. The transfer buffer contained 24 g of Tris base, 57.6 g of glycine and 800 ml of methanol. Water was added to make the solution up to 4 liters.

The nitrocellulose sheets were then rinsed with PBS/0.05% Tween 20 and placed in a tray containing Blotto buffer. The tray was gently shaken for two hours at room temperature. Blotto buffer consists of 50 g of non-fat dry milk, 1.0 g of antifoam A (optional), 0.1 g of merthiolate, and sufficient PBS to make a final volume of 1.0 liter. The buffer pH was adjusted to 7.0.

The nitrocellulose sheets where then rinsed in PBS/0.05% Tween 20 and dried on a paper towel between weighted plexiglass plates. The nitrocellulose sheets were then cut into strips 0.5 cm wide, each of which was numbered consecutively. The strips can either be used immediately or stored dry and in the dark for up to one month. The strips which carry the gp 120 band were to be used in the next stage.

The gp 120 nitrocellulose strips were then prepared to allow binding of monoclonal antibody to the protein bands. Forty of these strips were individually placed into an assigned slot of a slot tray and pre-soaked for twenty minutes in PBS/0.3% Tween 20. The pre-soak solution was aspirated into a Clorox™ containing trap. The strip wells was then rinsed once with PBS/0.05% Tween 20, the tray was shaken several times, and the solution was aspirated off.

The positive control was made of 2.0 ml of Blotto buffer/4% goat serum (which is made by mixing 100 ml of Blotto buffer and 4 ml of heat inactivated normal goat serum) added to one strip after which 10 microliters of heat activated AIDS patient serum was added to the well. 200 µl of supernatant was withdrawn from each of the thirty-nine wells in the microtiter plates which contained ELISA positive clones. Mixtures were made which consisted of 2.0 ml of supernatant, 5% non-fat dry milk, 50 microliters of 1 M HEPES (pH 8.0), and merthiolate.

The mixtures were then added to the strips and incubated overnight at room temperature. The mixture was then aspirated into a Clorox™ containing trap. The strips wells were rinsed once with PBS/0.05% Tween 20, rocked several times by hand, and aspirated with wash buffer. The strips were then washed three times with PBS/0.05% Tween 20, allowing five minutes for each rinse.

The strips were then reacted with the staining reagents, which permit visualization of specific antibody binding to gp 120. The reagent chosen was horseradish-peroxidase. This reagent exhibits color when contacted by a working substrate which consists of 10 ml of PBS, pH 7.4, 2.0 ml of substrate stock, and 4.0 microliters of 30% $H_2O_2$. Substrate stock is made by dissolving 0.3 g of 4-chloro-1-napthol in 100 ml of anhydrous methanol.

2.0 ml of Blotto/4% goat serum, containing 1:100 biotinylated goat anti-mouse IgG on biotinylated goat anti-human (for the positive control strip), was then added to each strip well. The trays were incubated at room temperature for thirty minutes on a rocking platform. The goat anti-mouse IgG conjugate will, of course, bind to any monoclonal antibody which has bound to the gp 120 on a strip.

The strip wells were then rinsed once with PBS/0.05% Tween 20, and shaken by hand several times to remove excess goat anti-mouse IgG conjugate. The wash buffer was discarded. The strip wells were then washed three times with PBS/0.05% Tween 20. Each washing lasted for five minutes.

2.0 ml of Blotto/4% goat serum containing 1:1000 horseradish-peroxidase-avidin D conjugate was added to each strip well. The avidin in this conjugate binds to the biotin in the goat anti-mouse IgG conjugate. Therefore the horseradish-peroxidase marker becomes linked to goat anti-mouse IgG and thereby marks any bound antibody. Following addition of the conjugate, the trays were incubated for thirty minutes at room temperature on a rocking platform.

Each strip well was washed three times with PBS/0.05% Tween 20, five minutes per wash, then once with PBS. 2.0 ml of the working enzyme substrate was added to each well, and the trays were incubated at room temperature until color developed. The working substrate solution contained 0.05% 4-chloro-1-naphthol and 0.01% $H_2O_2$ in phosphate buffer saline at pH 7.4.

(iii) Results

As discussed above, the Western blot analysis was performed using antibody from the thirty-nine ELISA positive wells. With Western blot analysis only antibody from six of these thirty-nine wells was found to react with gp 120. All six of these wells were among the seven wells which had been found immunofluorescence positive in the immunofluorescence assay. Thus, only one of the seven immunofluorescence positive clones was not also positive in Western blot analysis.

h) Production and Purification of Monoclonal Antibodies

To produce large quantities of desired monoclonal antibodies, the following procedure was performed.

The seven immunofluorescence positive clones, which have situated in the wells in the second twenty-four well plate, were grown up in a 100 mm tissue culture plate. The expanded culture of the selected seven single-cell clones were then separately injected into the peritoneal cavity of pristane treated mice, using five million cells per mouse. After seven days the ascites fluid of each mouse was collected and frozen.

The monoclonal antibodies in the ascites fluid were purified as follows. The frozen ascites fluid was thawed and filtered through a nylon cloth to remove viscous material. Sufficient phenylmethyl sulfonyl fluoride was added to the ascite fluid so that there was a final concentration of 0.1 mM. 0.05 ml of 1.2M acetate buffer (pH 4.0) was added for every milliliter of ascites fluid. The final concentration of the acetate buffer was 60 mM. The pH was adjusted to 4.5.

For every milliliter of treated ascites fluid, 25 microliters of caprylic acid (MW of 144.21, density of 0.91) was added dropwise with vigorous stirring. The suspension was kept at room temperature and stirred continuously for 30 more minutes.

The suspension was then centrifuged at 15,000 g for ten minutes in order to remove the precipitate. The supernatant, which contains IgG, was neutralized by adding a volume of 1 M HEPES buffer (pH 8.0) equal to one-tenth the volume of the supernatant. The IgG was then precipitated with 50% $(NH_4)_2SO_4$.

The precipitate was then dissolved in HEPES saline buffer. This solution was dialysed overnight against HEPES saline buffer in order to remove $(NH_4)_2SO_4$ from the IgG. The HEPES saline buffer was changed twice during the dialysis. After dialysis, the HEPES buffer saline contains purified dissolved IgG. The purified IgG was used in the infectivity assays and the syncytium formation assays which follow.

EXAMPLE II

Verifying the Efficacy of the Invention a) Neutralization Assay

An assay was performed to determine the effectiveness of the monoclonal antibodies of the invention in inhibiting infection of T-cells by HIV-1 virion. A comparison was made of the number of cells infected when HIV-1 alone was added to a cell culture, with the number infected when HIV-1 and the monoclonal antibodies of the invention were added. The cells selected for the neutralization assay were the H9 clones of the HT cell line.

i) Preparing the Virus, Antibody and Cells

H9 cells were prepared by washing a cell culture with H9 growth medium. The H9 growth medium contained 20% FBS (heat inactivated) in RPMI 1640, 5 mM of L-glutamine, 50 units/ml of penicillan, 50 mg/ml of streptomycin, and 5 mM of HEPES. The cells were then resuspended to a final concentration of $2\times10^6$ cells/ml. The suspension was then incubated with 2 micrograms/ml of polybrene in a water bath at 37° for twenty minutes.

After incubation, the cells were spun down at 700 g for seven minutes. The supernatant was then discarded, and the cells were resuspended in H9 growth medium and washed again to remove the polybrene. The cells were then resuspended to $2\times10^6$ cells/ml in growth medium.

Six of the seven immunofluorescence positive clones were chosen for use in the neutralization assay. The antibodies from the purified ascites (as describes above) were sterilized by passing them through a 0.22 micron Millipore filter. The solution was then diluted in the H9 growth medium to yield different final concentrations of 100, 10, 1, 0.1, and 0.01 micrograms/ml.

Virus at 20 $TCID_{50}$, or twenty times the $TCID_{50}$ value, was used in the infection of H9 cells. The $TCID_{50}$ value of the virus preparation was determined in previous infectivity assays under the same experimental conditions. It is defined as the virus titer at which 50% of the experimental wells are infected. 20 $TCID_{50}$ was equivalent to roughly a $4.72\times10^{-5}$ dilution of the viral stock.

In the infectivity assays, 30 microliters of virus suspension, and 30 microliters of each of the antibody solutions, were mixed in the wells of a microtiter plate at 4° C. for one hour. Each well was done in duplicate. The plate was then warmed in an incubator at 37° C. and 5% $CO_2$ for thirty minutes. 30 microliters of the polybrene treated H9 cell suspensions was then added to each well.

The microtiter plates were then incubated for one hour at 37° C. in an incubator. 110 microliters of the growth medium was added to each well, bringing the total volume to 200 microliters. The plates were incubated for three days, and new growth medium was replaced every three days. Cells were collected on the third, sixth, ninth and thirteenth day.

The identical procedure described above was also performed using murine monoclonal antibody to human chorionic gonadotropin (anti-HcG) rather than one of the anti-HIV-1 antibodies of the invention. The cells treated with the anti-HCG antibody served as a negative control.

ii) Immunofluorescence Assay of Infected Cells 100 microliter aliquots of the cell suspensions collected on days 9 and 13 were washed with 3 ml of PBS. The cell suspension was centriguted at 700 g for seven minutes and was washed again in PBS. The cells were finally resuspended in 50 microliters of PBS and 10 microliters of suspension was dotted onto a glass slide. This suspensions were air dried and then fixed with 1:1 acetone/methanol for ten minutes, air dried and stored at −20° C. before assay.

In the assay, the fixed cells were rehydrated in PBS for twenty minutes and then incubated with 5% normal goat serum in PBS for another thirty minutes. After dripping away the excess normal goat serum, the cells were incubated at room temperature for one hour with anti-p24 monoclonal antibody (at a dilution of 1:100) containing 2% normal goat serum. This antibody binds specifically to the p24 core protein of HIV-1. The slides were kept in the humidifier to avoid drying. After the incubation, the slides were rinsed for three times in PBS for a total of 30 minutes. Then fluorescein conjugated goat anti-mouse IgG (F(ab')$_2$) fragment was added at a dilution of 1:20. The slides were incubated for one hour at room temperature. The slides were then rinsed in three changes of PBS for thirty minutes and counterstained with 0.5% Evans blue for five minutes, washed and mounted in Fluoromount G. The cells were then observed under a fluorescence microscope.

The number of infected cells were counted at the magnification of 400×. Four data points were collected from each slide by random sampling over the field.

iii) Results

The results are depicted graphically in FIGS. 1 and 2, where the percentage of immunofluorescence cells is plotted against the concentration of antibody in suspension. The results in FIG. 1 are from cells collected on day 9. In FIG. 2 the cells were collected on day 13.

Turning to FIGS. 1 and 2, it can be seen that four of the six antibodies tested (designated as BAT 123, 267, 509, and 085) were effective in inhibiting infection. In particular, BAT123 showed almost complete inhibition of infection on day 9. This results is to be contrasted with the negative control anti-HcG antibody, which exhibited virtually no inhibition. Nearly 100% of the cells treated with anti-HcG were immunofluorescent, irrespective of the concentration of antibody. The similar result was obtained with monoclonal antibody BAT 496 which is reactive with gp 120 but shows no neutralization activity. For this reason, BAT 496 was not assayed on day 13 and does not appear in FIG. 2.

It should be noted that another antibody, BAT401, was tested for neutralization. However, the results do not appear in FIGS. 1 and 2 because it was found less effective in syncytium formation inhibition.

A comparison of FIGS. 1 and 2 shows that as time goes on, more of the cells in the suspension become infected. This result is expected. The amount of antibody in suspension available to neutralize the virus is decreasing due to change in medium and probably degradation or internalization. However, the infected H9 cells continually produce more virus, and this virus eventually infects all the cells.

The plots in FIGS. 1 and 2 show that with a decreasing concentration of antibody, a greater number of cells are infected. This indicates that the neutralizing effect of the antibodies is dosage dependent. The $IC_{50}$ value of each monoclonal antibody, which is the dosage at which 50% of the cells are infected, was calculated. The results as taken on day 9 appear below in Table I.

TABLE I

| Monoclonal Antibodies | $IC_{50}$ |
|---|---|
| Anti-HcG (Negative Control) | $1 \times 10^5$ ng/ml |
| BAT085 | 100 ng/ml |
| BAT123 | <<10 ng/ml |
| BAT267 | <10 ng/ml |
| BAT509 | 30 ng/ml |
| BAT496 | $1 \times 10^5$ ng/ml |

It can be seen that the monoclonal antibodies which are most effective at inhibition (BAT 123, 267 and 509), do so in nanogram quantities. This indicates that these monoclonal antibodies may also be very effective in minute quantities for in vivo AIDS therapy. The use of such minute doses would be a significant advantage over known therapeutic agents.

b) Inhibition of Syncytium Formation

Another test for the monoclonal antibodies of the invention was to determine whether they inhibited syncytium formation. Inhibition of syncytium formation would enhance the therapeutic value of the antibodies, inasmuch as the majority of cell infection and cell death in vivo is believed to occur via syncytium.

The syncytium assay was based on the assumption that the exterior envelope protein of the virus in infected H9 cells binds to the CD4 antigen which is carried by T cells. In the assay, infected H9 cells are added to a well containing CD4 DNA transfected HeLa cells. HeLa cells are used because they adhere, in a monolayer, to the bottom of the well. These transfected HeLa cells express abundantly CD4 antigen on their cell surface. Thus, they have the ability to fuse with infected H9 cells. Therefore, if syncytium formation occurs, aggregates of HeLa and H9 cells will be bound to the well. These multi-nucleated giant cells can readily be observed and counted.

The protocol for the syncytium formation assay is set forth below.

(i) Procedure for Syncytium Formation Assay

HeLa T4 cells (which express the CD4 antigen on the surface) were grown in a HeLa-T4 growth medium, which contained 5% FBS (heat inactivated) in DMEM, 5 mM L-glutamine, 50 units/ml of penicillin, 50 mg/ml of streptomycin, and 5 mM of HEPES. The cells were harvested by trypsinization, to remove the cells from the flask, and washed. The cells were then seeded onto a 96 wells microtiter plate at a density of 10,000 cells per well. The plates were incubated at 37° C. for thirty-six hours until 90% confluency was reached.

Both infected and uninfected H9 cells were then prepared. For preparing these cells, the cell suspension was first washed twice with H9 growth medium (20% FBS in RPMI 1640, 5 mM of L-glutamine, 50 units/ml of penicillin, 50 mg/ml of streptomycin and 5 mM of HEPES.) The cells were then resuspended in HeLa-$T_4$ at a concentration of 0.4 million/ml.

The antibodies were prepared by first performing a sterile filtration on the seven antibody solutions which had been used in the neutralization assay. Six of these solutions contained antibodies of the invention, and the seventh contained the anti-HcG. Each solution was then diluted to make two final concentration of 1.0 and 10 micrograms/ml.

50 microliters of each antibody solution and 50 microliters of infected H9 cell suspension was added to the various wells of the microtiter plate. The microtiter plate wells had previously been coated with the HeLa T4 cells. In another HeLa T4-coated well, infected H9 cell suspension was added without the addition of antibody. This well was to serve as a positive control. In yet another coated well, uninfected H9 cell suspension was added. This well was to serve as a negative control. The experiments were done in triplicate.

The plates were then incubated for eighteen hours at 37° C. and 5% $CO_2$. The plates were washed gently twice with DMEM in order to remove unattached H9 cells. The DMEM was removed and the cells were fixed by adding 200 microliters of methanol per well for seven minutes. After removing the methanol, the cells were air dried, and then stained with 100 microliters of 1.4% methylene blue for ten minutes. The cells were rinsed with distilled water three times.

After staining, the cells were then observed under an inverted microscope (at a magnification of 100 times), and the number of syncytia per field was determined. Aggregates of cells were considered to be a syncytium if more than five nuclei were present. Each well was counted three time randomly.

(ii) Results

The negative control well showed no syncytium formation. The results for the remainder of the wells appear below in Table II, expressed as a mean±standard deviation.

TABLE II

Inhibition of Syncytium Formation Between HIV-infected H9 Cells and HeLa $T_4$ Cells

| Antibody* & Concentration | | Number of Syncytia per Field | % Inhibition |
|---|---|---|---|
| None | | 54.8 ± 3.6 | 0 |
| Anti-HcG | 1 | 50.0 ± 5.1 | 8.7** |
| | 10 | 54.7 ± 7.6 | 0 |
| BAT085 | 1 | 39.7 ± 2.8 | 27.6 |
| | 10 | 41.3 ± 6 | 24.6 |
| BAT123 | 1 | 30.3 ± 4.5 | 44.7 |
| | 10 | 15.3 ± 4.7 | 72.0 |
| BAT267 | 1 | 41.0 ± 6.6 | 25.2 |
| | 10 | 27.3 ± 5.7 | 50.2 |
| BAT509 | 1 | 41.7 ± 4.9 | 23.9 |
| | 10 | 28.3 ± 3.3 | 48.5 |
| BAT496 | 1 | 56.3 ± 9 | 0 |
| | 10 | 52.0 ± 3.6 | 5.1** |

*The 1.0 microgram/ml and the 10 microgram/ml solutions of antibody are designated "1" and "10" respectively.
**Not significantly different from negative control.

It can be seen from Table II that these results suggest that screening by the above-described methods is essential to identify the best antibodies for therapeutic use. The same antibodies which lowered infectivity of free HIV-1 virions (as shown in FIGS. 1 and 2) also were effective in inhibiting syncytium formation. BAT 123, 267 and 509 were particularly effective in both applications. BAT 496 was almost ineffective in both applications as was, of course, the negative control anti-HcG. Although BAT 085 was effective in neutralization, it was not among the most effective in syncytium inhibition.

BAT401 was not very effective at syncytium inhibition, although it was effective in the neutralization assay. This result indicates that antibodies which are effective in inhibiting HIV-1 infection are not necessarily effective in inhibiting syncytia formation. Accordingly, the three monoclonal antibodies of invention which were most effective (BAT123, 264 and 509) at inhibiting both infectivity by the HIV-1 virions and syncytium formation, were deposited at the American Type Culture Collection in Rockville, Md. They are available for inspection by the Patent and Trademark Office during the pendency of this application.

The Table II results demonstrate that, similar to neutralization as shown in Table I, syncytium inhibition is also dosage-dependent. The solutions with 10 microgram/ml of antibody were generally more effective in inhibition than the 1 microgram/ml solutions.

EXAMPLE III

Neutralization of Different Strains and Isolates of HIV-1

Several antibodies were found to inhibit the infectivity of free HIV-1 virions and the syncytium formation between HeLa-CD4+ cells and H9 cells infected by HIV-1B. Since genomic analyses indicate that the virus mutates significantly both in vivo and in vitro (Alizon, M., Wain-Hobson, S., Montagnier, L. and Sonigo, P. (1986) Cell 46:63–74; Starcich, B. R., Hahn, B. H., Shaw, G. M., McNeely, P. D., Modrow, S., Wolf, H., Parks, E. S., Parks, W. P., Josephs, S. F., Gallo, R. C. and Wong-Staal, F. (1986) Cell 45:637–648), the application of these neutralizing monoclonal antibodies as agents for therapy and protection relies heavily on whether they are group-specific and protect HIV-1 infection caused by a large proportion of strains of the virus in the population. It is important to know whether BAT 123 and the other neutralizing monoclonal antibodies we raised recognize one or more distinct neutralization epitopes in the viral envelope protein gp120 with conserved amino acid sequences among different strains of HIV-1. In order to understand these characteristics of the antibodies, we studied whether these antibodies can inhibit the syncytium formation by other strains of HIV-1 with a substantial degree of heterogeneity in the amino acid sequence of gp120 (RF, AL, MN, Z84 and Z34) (Starcich et al., supra.). The neutralization antibody BAT 123 was chosen in the study because it was shown to elicit highest potency in the neutralization of the virus. In order to evaluate the effectiveness of the neutralizing antibodies on different HIV-1 variants existing in the infected population, we collected blood specimen randomly from infected individuals (in Houston, Tex.; in Los Angeles, Calif.; and in Boston, Mass.) with different disease states, and examined the effect of BAT 123 on the viral infection in the lymphocyte preparations by co-culture experiments.

a) Syncytium formation assay

Syncytium formation assay was performed as described in Example 2.

b) Co-culture assay

The procedure used is similar to that described earlier, 30 ml of heparinized blood from each patient was freshly collected and processed for mononuclear leukocytes by density-gradient centrifugation. Briefly, the whole blood was diluted with equal volume of phosphate-buffered saline (PBS). 25 ml of the diluted blood was laid over 10 ml of Ficoll-Paque (Pharmacia) and centrifuged at 1500×g for 30 minutes; at the end of the centrifugation, the interphase containing mononuclear leukocytes was removed and washed twice in PBS. The mononuclear leukocytes were then cultured at $0.5-1\times10^6$/ml in the RPMI 1640 medium supplemented with 15% heat-activated fetal bovine serum, 2 mM L-glutamine, 10% interleukin-2 (Cellular Products), 25 neutralizing units/ml sheep anti-human alpha interferon (Interferon Science), 100 units/ml penicillin, 100 ug/ml streptomycin and 2 ug/ml Polybrene. Equal volume of phytohaemagglutinin (PHA)-stimulated mononuclear leukocytes from normal donor blood was mixed with the patient culture. The mononuclear leukocytes from the normal donor blood was stimulated for one day early with 2 ug/ml PHA-P (Sigma). They were washed twice in PBS to remove the lectin. BAT 123 was added to the test culture at the final concentration of 10 ug/ml. The total volume of the culture was 10 ml. Five ml of the cell culture was removed at 3–4 day intervals, centrifuged at 1,500×g for 15 minutes to remove the cells and debris. The supernatants were collected and assayed for reverse transcriptase activities after precipitation of the virus using 10% polyethylene glycol (PEG) (Gupta, P., Galachandran, R., Grovit, K., Webster, D. and Rinaldi, C. Jr. (1987) J. Clin. Microbiology 25:1122–1125).

c) Reverse transcriptase assay

The procedure for the measurement of reverse transcriptase activity was described earlier (Barre-Sinoussi, F., Chermann, J. C., Rey, F. Nugeyre, M. T., Charmaret, S., Gruest, J., Daugnet, C. Axler-Blin, C., Vezinet-Brun, F., Ronziou, C., (1984) Science 220:86–87). Briefly, the PEG-precipitated virus was solubilized for 20 minutes in 100 ul of Tris-buffered saline (pH 8.2) containing 0.1% Triton X-100, 2 mM dithiothreitol, 0.2 mM leupeptin and 50 mM ε-amino-n-caproic acid. In the assay, 100 ul of the substrate solution in 50 mM Tris-HCl pH 8.2 containing 8 mM $MgCl_2$, 20 $\mu$Ci $^3$H-thymidine triphosphate (2 mCi/ml), 0.05 units of template-primer poly(rA).p(dT)$_{12-18}$ was added to 25 ul of the solubilized virus. No template-primer was added to the corresponding control, but substituted with distilled water instead. The reaction mixtures were incubated at 37° C. for one hour and the reaction was terminated by addition of 5% cold trichloracetic acid and finally filtered over Whatman GF/C filters which were washed thoroughly and counted for radioactivity using a scintillation counter. The specific reverse transcriptase activities were calculated as the difference in radioactivity when the template-primer was added.

Results & Discussion

We studied the neutralizing monoclonal antibodies claimed with regard to their group-specificity to the virus and their cross-protection to six different HIV-1 strains (HIV-$1_B$, HIV-$1_{RF}$, HIV-$1_{AL}$, HIV-$1_{MN}$, HIV-$1_{Z84}$, and HIV-$1_{Z34}$). In syncytium formation assay between HeLa-CD4+ cells and H9 cells chronically infected with these strains of HIV-1 respectively, BAT 123 at 25 ug/ml inhibited syncytium formation by almost 80%. It also reduced the syncytium formation of H9 cells infected with HIV-$1_{MN}$, HIV-$1_{AL}$, HIV-$1_{RF}$ and HIV-$1_{Z34}$ by approximately 50%, and HIV-$1_{Z84}$ by 23%. (See Table III).

TABLE III

CROSS-PROTECTION OF SYNCYTIUM FORMATION BY
H9 CELLS INFECTED WITH DIFFERENT HIV-1 STRAINS

| Infected H9 Cells | With Antibody | Without Antibody | % of Inhibition |
|---|---|---|---|
| H9 uninfected (control) | — | — | — |
| H9 - HIV - $1_B$ | 2.33 ± 0.51* | 10.25 ± 0.99 | 77.3 |
| - HIV - $1_{MN}$ | 2.08 ± 0.38 | 4.25 ± 0.46 | 51.0 |
| - HIV - $1_{AL}$ | 7.08 ± 0.66 | 13.91 ± 1.27 | 49.1 |
| - HIV - $1_{RF}$ | 1.91 ± 0.55 | 3.91 ± 0.47 | 51.0 |
| - HIV - $1_{Z84}$ | 12.41 ± 1.46 | 16.08 ± 0.55 | 22.8 |
| - HIV - $1_{Z34}$ | 1.58 ± 0.14 | 3.08 ± 0.55 | 48.7 |

*Expressed as number of syncytia per microscopical field (x ± S.E., n = 11 or 12), p < 0.05, paired student's t test.

In the co-culture experiments using lymphocytes isolated from the peripheral blood of patient clinically diagnosed positive asymptomatic state, AIDS or ARC; out of 32 patient blood specimen tested, the virus had been isolated from 18 samples as measured for reverse transcriptase activities. When 10 ug/ml BAT 123 was added in the culture medium throughout the experiments, the viral replication was inhibited in all of the 18 virus-positive cultures. The degree of inhibition ranged from 43.7 to 100%. Among the 18 samples, 8 samples were effectively inhibited by over than 90%. (See Table IV).

The results from our in vitro experiments suggest that the neutralizing monoclonal antibody BAT 123 is group-specific and can cross-protect different diverse strains of HIV-1 in the syncytium formation assays and inhibit viral infection in patient blood specimen.

CO-CULTURE EXPERIMENTS
Reverse Transcriptase Activity (cpm)

| Patient No. | Control | With BAT123 | Percent Inhibition | T4 Cell Count/μl | Total Lymphocyte/μl | Clinical States |
|---|---|---|---|---|---|---|
| 7 | 720123 | 335156 | 53.4 | 180 | 2250 | +, asym |
| 8 | N.D.* | | | 398 | 1443 | ARC |
| 9 | N.D. | | | 180 | 2178 | +, asym |
| 10 | 100825 | 38283 | 62.0 | 0 | 5044 | AIDS (PCP) |
| 11 | 331689 | 186660 | 43.7 | 110 | 2210 | AIDS (PCP) |
| 12 | 31707 | 104 | 99.9 | 14 | 462 | AIDS (PCP, KS) |
| 13 | N.D. | | | 261 | 1440 | ARC |
| 14 | N.D. | | | 23 | 2310 | AIDS (PCP) |
| 15 | 9081 | 0 | 100.0 | 229 | 1590 | AIDS (PCP) |
| 16 | 66224 | 14382 | 72.4 | 29 | 400 | AIDS (PCP) |
| 17 | 65991 | 5593 | 91.5 | 25 | 2553 | ARC |
| 18 | N.D. | | | 715 | 3502 | ARC |
| 19 | N.D. | | | 825 | 2886 | +, asym |
| 20 | N.D. | | | 948 | 2964 | ARC |
| 21 | N.D. | | | 151 | 1892 | ARC |
| 22 | 22034 | 829 | 96.2 | 171 | 2444 | AIDS (PCP) |
| 23 | 76103 | 1004 | 98.6 | 140 | 870 | AIDS (PCP) |
| 24 | N.D. | | | 503 | 2400 | +, asym |
| 25 | 166167 | 10900 | 93.4 | 163 | 3264 | AIDS (PCP) |
| 26 | 171670 | 66576 | 61.2 | 74 | 530 | +, asym |
| 27 | 293485 | 143301 | 51.1 | 8 | 2016 | AIDS |
| 28 | 16884 | 146 | 99.1 | 33 | 1050 | AIDS |
| 29 | 38703 | 9104 | 76.0 | 197 | 1364 | AIDS |
| 30 | 20863 | 1298 | 93.8 | 178 | 3570 | AIDS |
| 31 | N.D. | | | 168 | 2808 | AIDS |
| 32 | 284570 | 102787 | 63.9 | 265 | 3716 | AIDS |
| 33 | N.D. | | | 30 | 594 | AIDS |
| 34 | Blood not processed** | | | 33 | 1664 | AIDS |
| 35 | N.D. | | | 721 | 4200 | +, asym |
| 36 | N.D. | | | 723 | 2784 | +, asym |
| 37 | 43108 | 14062 | 67.4 | 42 | 4355 | +, asym |

-continued

CO-CULTURE EXPERIMENTS
Reverse Transcriptase Activity (cpm)

| Patient No. | Control | With BAT123 | Percent Inhibition | T4 Cell Count/µl | Total Lymphocyte/µl | Clinical States |
|---|---|---|---|---|---|---|
| 38 | N.D. | | | 516 | 3036 | +, asym |
| 39 | 50256 | 8019 | 84.0 | 10 | 350 | AIDS |

*N.D. = Not detected
**Specimen from VA-34 was not processed since there was not enough blood.
asym = asymptomatic
AIDS = acquired immunodeficiency syndrome
ARC = AIDS related complex
PCP = *Pneumocystic carinii* pneumonia
KS = Kaposi's sarcoma

EXAMPLE IV

Determining the Peptidic Segments of Gp120 Reactive With Monoclonal Antibodies Methods In order to map the eptioeps on gp120 of HIV-1 that are recognized by the monoclonal antibodies, we have determined using Western blot assays the reactivities of some of the monoclonal strips. The strips were obtrained from Dr. Steve Petteway, Medical Products Department, DuPont de Nemours and Company, Wilmington, Del. The synthetic peptides on the strips are 8–20 amino acid residue long. These peptides represent overlapping peptidic segments across the entire length of gp120 of HIV-1B strain. Several tens of peptide solutions had been adsorbed on individual strips in equally spaced regions and the strips were provided to us in a dry form.

The immunoblotting procedure using the nitrocellulose strips is the same as the Western blot procedure used to determine whether the monoclonal antibodies react with gp120 described in the preceding section.

Results

Three of the monoclonal antibodies BAT123, BAT267, and BAT085 showed very clear and specific reactivities with particular peptides in the Western blot assay.

BAT267 RPNNNTRKSIRIQRG (residue #298–312)

BAT123 RIQRGPGRAFVTIGK (residue #308–322)

BAT08 VQKEYAFFYKLDIIP (residue #169–183)

The 15 amino acid long peptides reactive with BAT267 and BAT123 overlap by 5 amino acids. However, the antibodies react with just one of them and do not react with the other to any measurable extent. The antibodies do not react with peptides overlapping at the other ends either, i.e. BAT267 does not react with LNQSVRINCTRPNNN and BAT123 does not react with VTIGKIGNMRQAHCN. These results suggest that the antibodies react with an epitope borne by either all or a part of the middle five amino acids or a combination of these amino acids with some of the flanking amino acids. Similar findings have been made for BAT085 and similar conclusions may be made for it.

Equivalents

Those skilled in the art will recognize, or be able to ascertain using no more than routine experimentation, many equivalents to the specific embodiments of the invention described herein. These and all other equivalents are intended to be encompassed by the following claims.

What is claimed is:

1. A chimeric immunoglobulin comprising an antigen binding region of the murine immunoglobulin BAT123 or an immunoglobulin which specifically binds to the same epitope as BAT123 and a human constant region.

2. A chimeric monoclonal immunoglobulin having a variable region of rodent origin and a constant region of human origin which binds to an epitope within a peptide including amino acid residue numbers 308 to 322 of gp120 of HIV-$1_B$, as designated by the numbering system set forth in Human Retroviruses and AIDS 1990, Los Alamos National Laboratory (Eds. Myers, G. et al.).

3. A chimeric monoclonal immunoglobulin having a variable region of rodent origin and a constant region of human origin which binds to the amino acid sequence RIQRGPGRAFVTIGK.

* * * * *